US012629135B2

(12) United States Patent
Ranjbar et al.

(10) Patent No.: US 12,629,135 B2
(45) Date of Patent: May 19, 2026

(54) CARDIAC IMAGING MACHINERY BASED ON ULTRASOUND METHODS

(71) Applicants: Saeed Ranjbar, Tehran (IR); Mersedeh Karvandi, Tehran (IR); Arash Mohammadi Tofigh, Tehran (IR)

(72) Inventors: Saeed Ranjbar, Tehran (IR); Mersedeh Karvandi, Tehran (IR); Arash Mohammadi Tofigh, Tehran (IR)

( * ) Notice: Subject to any disclaimer, the term of this patent is extended or adjusted under 35 U.S.C. 154(b) by 626 days.

(21) Appl. No.: 18/104,987

(22) Filed: Feb. 2, 2023

(65) Prior Publication Data

US 2024/0000433 A1     Jan. 4, 2024

Related U.S. Application Data

(60) Provisional application No. 63/344,778, filed on May 23, 2022.

(51) Int. Cl.
| | |
|---|---|
| *A61B 8/08* | (2006.01) |
| *A61B 8/00* | (2006.01) |
| *G06T 7/00* | (2017.01) |

(52) U.S. Cl.
CPC ............ *A61B 8/483* (2013.01); *G06T 7/0012* (2013.01); *G06T 2207/30048* (2013.01)

(58) Field of Classification Search
CPC ....... A61B 8/483; A61B 8/463; A61B 8/5223; A61B 8/0883; G06T 7/0012; G06T 2207/30048
See application file for complete search history.

(56) References Cited

U.S. PATENT DOCUMENTS

| | | | | |
|---|---|---|---|---|
| 2006/0224062 A1* | 10/2006 | Aggarwal | ......... | G01R 33/5673 600/413 |
| 2010/0329521 A1* | 12/2010 | Beymer | ............... | G06V 10/761 600/443 |
| 2011/0182352 A1* | 7/2011 | Pace | .................... | H04N 19/543 375/240.1 |
| 2013/0116561 A1* | 5/2013 | Rothberg | ............. | A61B 8/4477 600/459 |
| 2017/0116728 A1* | 4/2017 | Codella | .................. | G16H 50/30 |
| 2017/0124701 A1* | 5/2017 | Liang | ................... | A61B 8/5223 |
| 2020/0178939 A1* | 6/2020 | Song | .................... | A61B 8/5223 |

* cited by examiner

*Primary Examiner* — Iriana Cruz
(74) *Attorney, Agent, or Firm* — Patent 360; Barry Choobin

(57)     ABSTRACT

A system and method for human heart modelling to create a dynamic virtual model of heart that can be used for diagnosis and determining suitable therapy. The dynamic virtual model can be created using 2D or 3D echo images or video clips obtained from ultrasound reversal wave data. Arbitrary pixels or voxels in the echo images are tracked phase-by-phase per cardiac cycle. From this, original reversal wave equation $\rho_p$ attached to the arbitrary pixel or voxel is obtained. Then is generated a deformable map $f_p$ with an equation of curve passed from the arbitrary pixel or voxel within the cardiac cycle determined by solving Lagrange-Euler equations. Finally, new 2D or 3D images with improved spatial resolution can be obtained that are used for the human heart modelling.

16 Claims, 24 Drawing Sheets

402   404   406   408   410

422   424   426   428   430

502

504    506

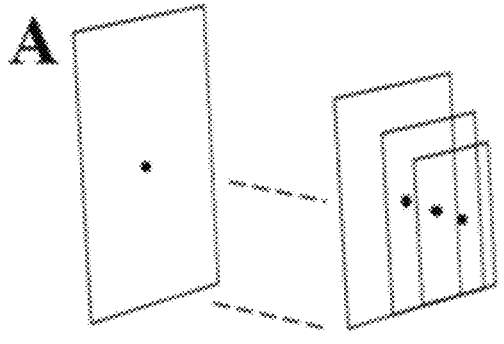
A
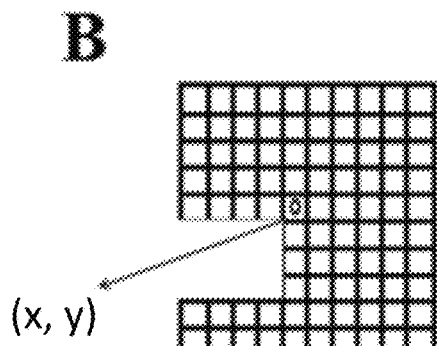
B
(x, y)
Fig. 7A                    Fig. 7B
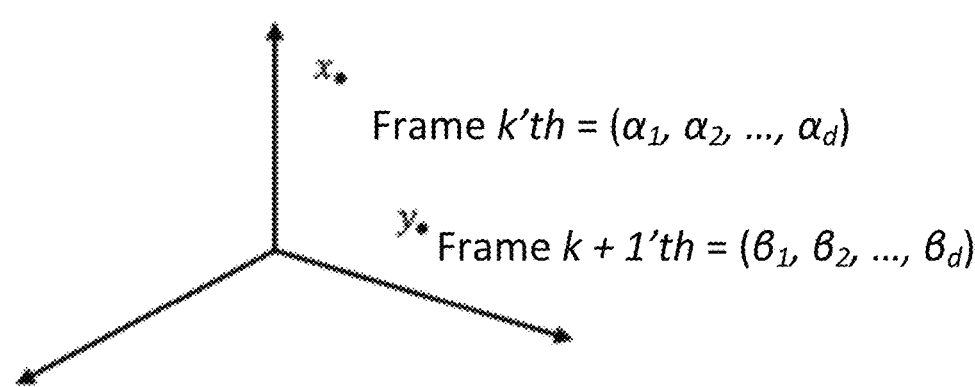
Frame $k'th = (\alpha_1, \alpha_2, ..., \alpha_d)$
Frame $k + 1'th = (\beta_1, \beta_2, ..., \beta_d)$
Fig. 8

$$\nabla_{u(p,t_1)} = \varepsilon_{p,t_1} \times v_{p,t_1} = \begin{bmatrix} \varepsilon_{p,,t_1}11 & \cdots & \varepsilon_{p,,t_1}13 \\ \vdots & \ddots & \vdots \\ \varepsilon_{p,,t_1}31 & \cdots & \varepsilon_{p,,t_1}.33 \end{bmatrix} = v(p,t_2)$$

CARDIAC IMAGING MACHINERY BASED ON ULTRASOUND METHODS

CROSS-REFERENCE TO RELATED APPLICATIONS

This application claims priority from a U.S. Provisional Patent Appl. No. 63/344,778 filed on May 23, 2022, which is incorporated herein by reference in its entirety.

FIELD OF INVENTION

The present invention relates to a system and method for medical imaging, and more particularly, the present invention relates to a system and method for cardiac imaging using ultrasonic waves.

BACKGROUND

For decades automotive, aerospace, and energy industries have used advanced simulation technology to virtually design, test and validate their products before they are built. Built on these successes, there has been a profound interest in medical sciences to use virtual simulation for designing, testing, and validating new treatment modalities. Of particular interest are modelling cardiovascular disease as it represents the primary cause of mortality in the industrialized nations. The heart is the most vital and complex organ of the human body controlled by the interplay of anatomical, electrical, and biomechanical events.

In the past three decades, there has been a concerted effort in human heart modelling for a variety of reasons including facilitating the clinical decision-making process and guiding in the treatment planning and acceleration process. Despite these efforts, there remains a significant barrier in applying virtual human heart models in clinical applications. The primary reason is that the known virtual simulation models are engineering models that are based on medical images (anatomical data) combined with clinical measurement data. The clinical measurement data comes from variety of invasive and non-invasive modalities that capture the biomechanical events for multi-scale computational modelling. Most of these models have also been developed and validated using data from invasive measurements in controlled conditions in animal models. These models are useful for demonstrating the proof of concept and development of general models. However, such models are not useful in human heart modelling for individualized prediction of different treatment modalities with the goal of virtually selecting the most promising treatment within the paradigm of Personalized Medicine.

For patient-specific human heart modelling, the challenge is to fuse the patient-specific geometrical data retrieved from imaging modality with real-time in-plane biomechanical data of these geometrical points. All imaging platforms convert physical data into image data. Until now, scientists have focused on the acquisition of better images or on post-processing techniques to increase spatial and temporal resolution.

A need is appreciated for a system and method for retrieval and fusion of geometrical data with in-plane biomechanical data from any echocardiographic dataset through cardiac cycle of any anatomical point for patient-specific heart modelling.

BRIEF DESCRIPTION OF THE DRAWINGS

The accompanying figures, which are incorporated herein, form part of the specification and illustrate embodiments of the present invention. Together with the description, the figures further explain the principles of the present invention and enable a person skilled in the relevant arts to make and use the invention.

3

Differences and comparisons by multiplying steps 4, 6, 8 and 10 between two fixed volumes; fifth row shows 3D high intensity resolution increase by applying the Hadamard transformation on the new volumes.

FIG. 7A shows the frame; FIG. 7B shows a movie made by gluing the number of frames together.

FIG. 8 illustrates each frame placed in a space of high dimensions as N-tuples of pixels.

Figure 9:
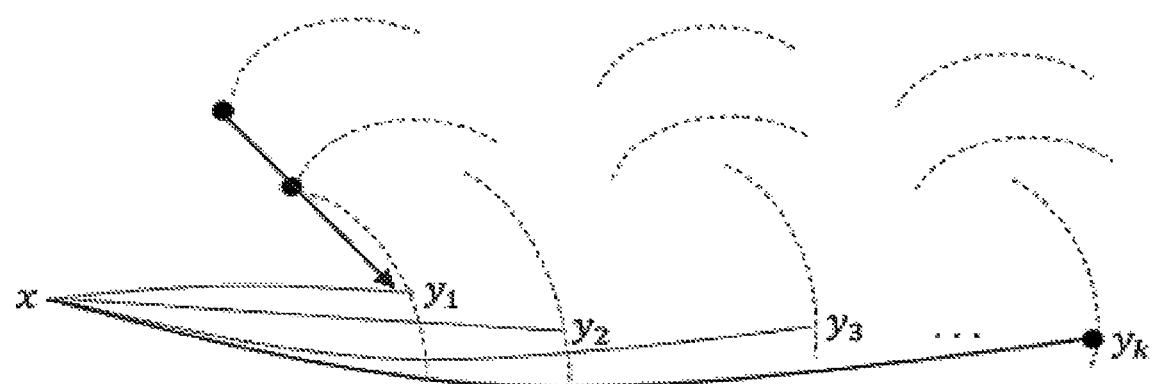

FIG. 9 illustrates a schema in which x represents a frame, with y1 being the closest point to x, the first neighborhood being B1 (x) (a Sphere with center "x" and the radius with distance value between x, y1) and y2 being the closest point after y1 to point x, which makes the second neighborhood B2 (x), and so on until neighborhood k-th so to reach to the nearest anatomical point to x.

Figure 10:
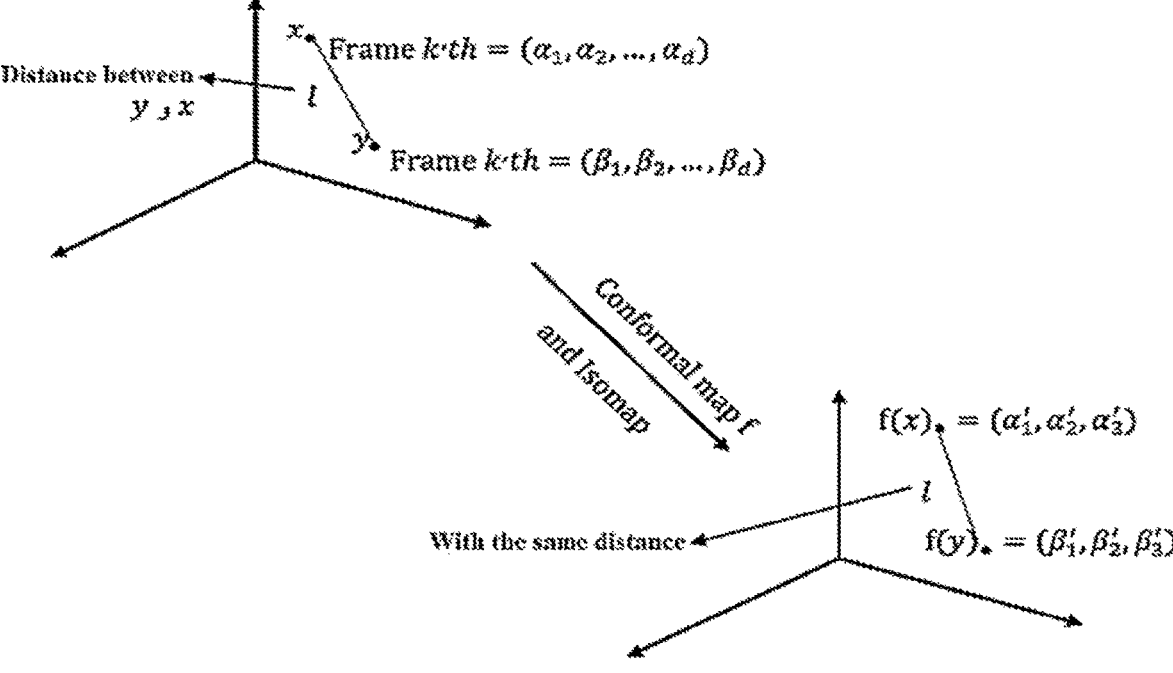

FIG. 10 shows mapping "f" from N-dimensional space to a 3D Cartesian space that preserves distances (Iso-map f) and angels (conformal map f) and compatible with trajectories obtained by the Lagrange equations.

Figure 11:
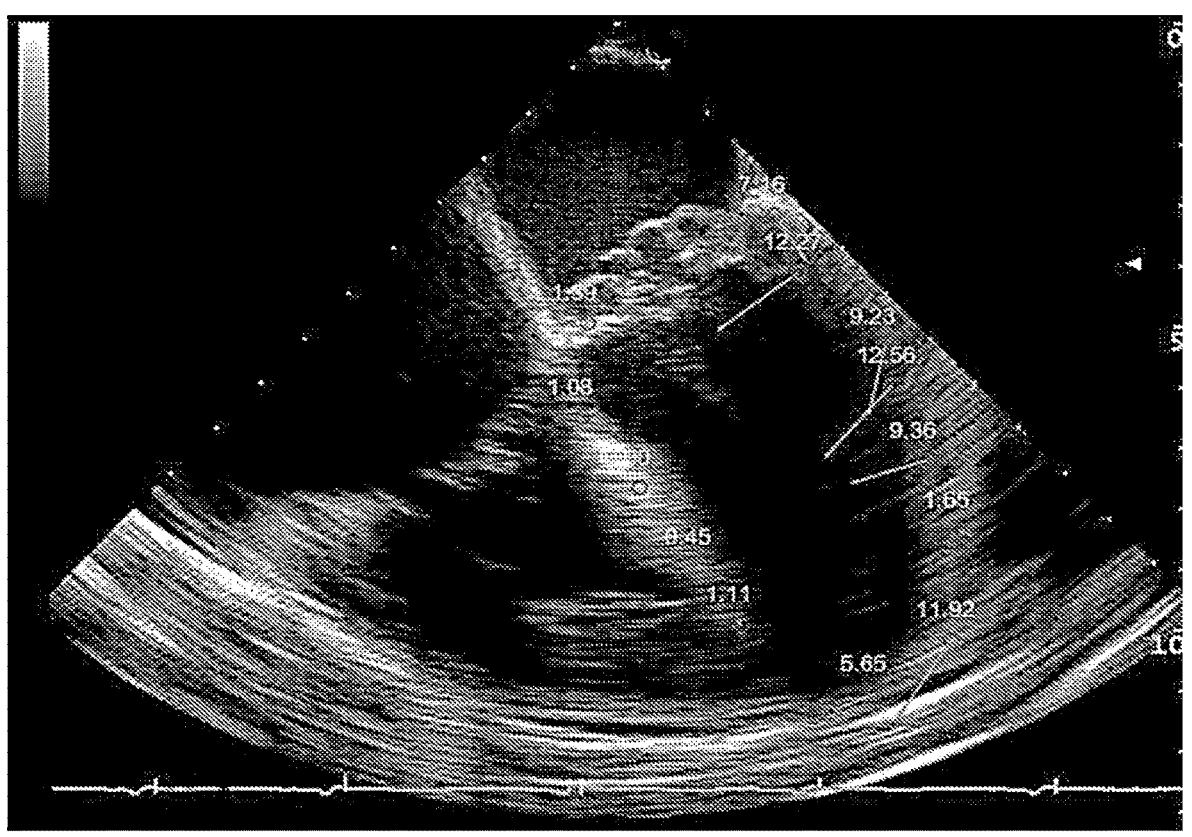

FIG. 11 shows the vector velocities with numerical values (mm/s) fused with geometrical points through cardiac cycle.

Figure 12:
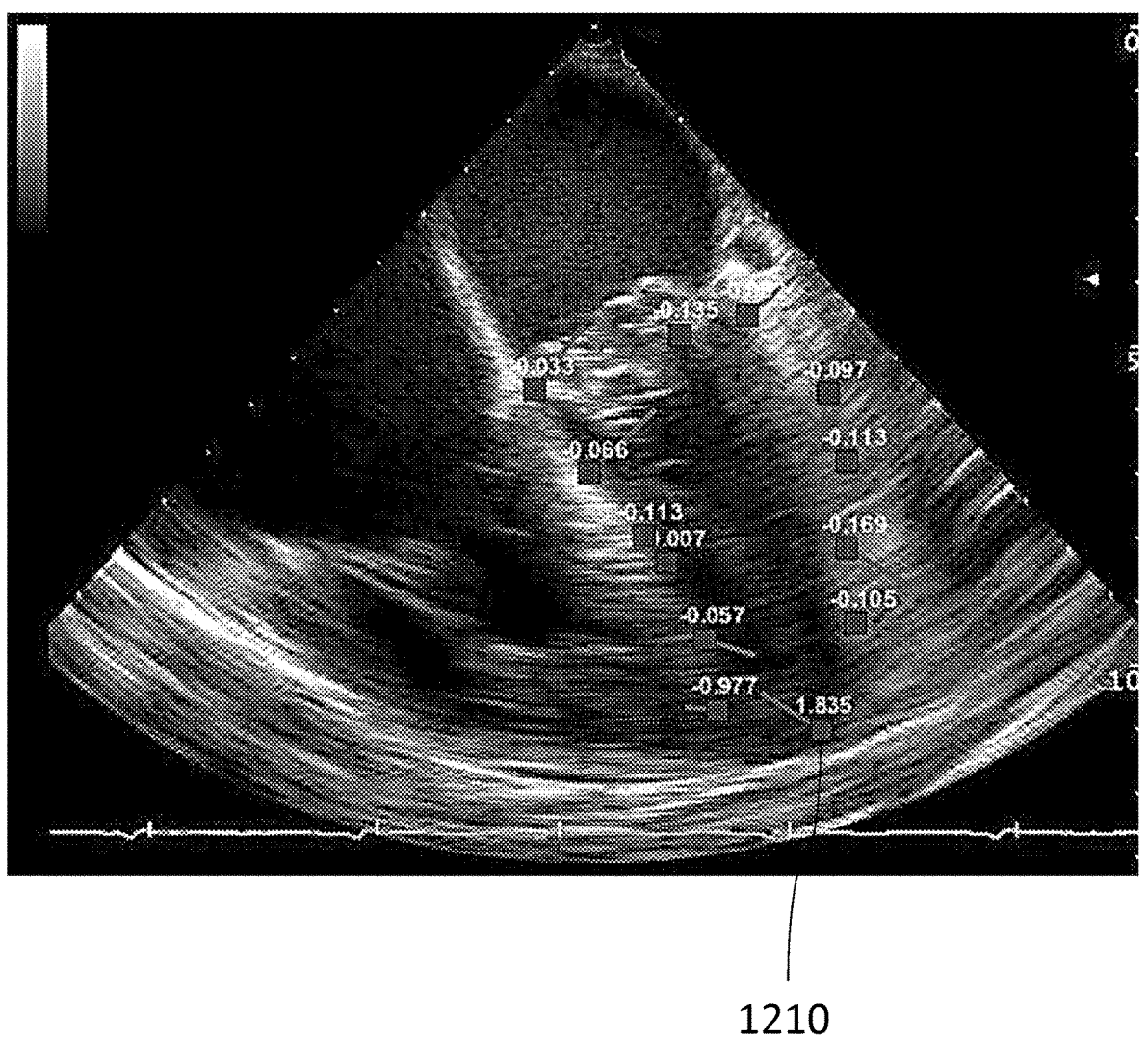

FIG. 12 shows the strain vectors and their numerical values coded with color (grey boxes 1210 in the drawings which can be colored red, the red indicates negative values).

Figure 13:
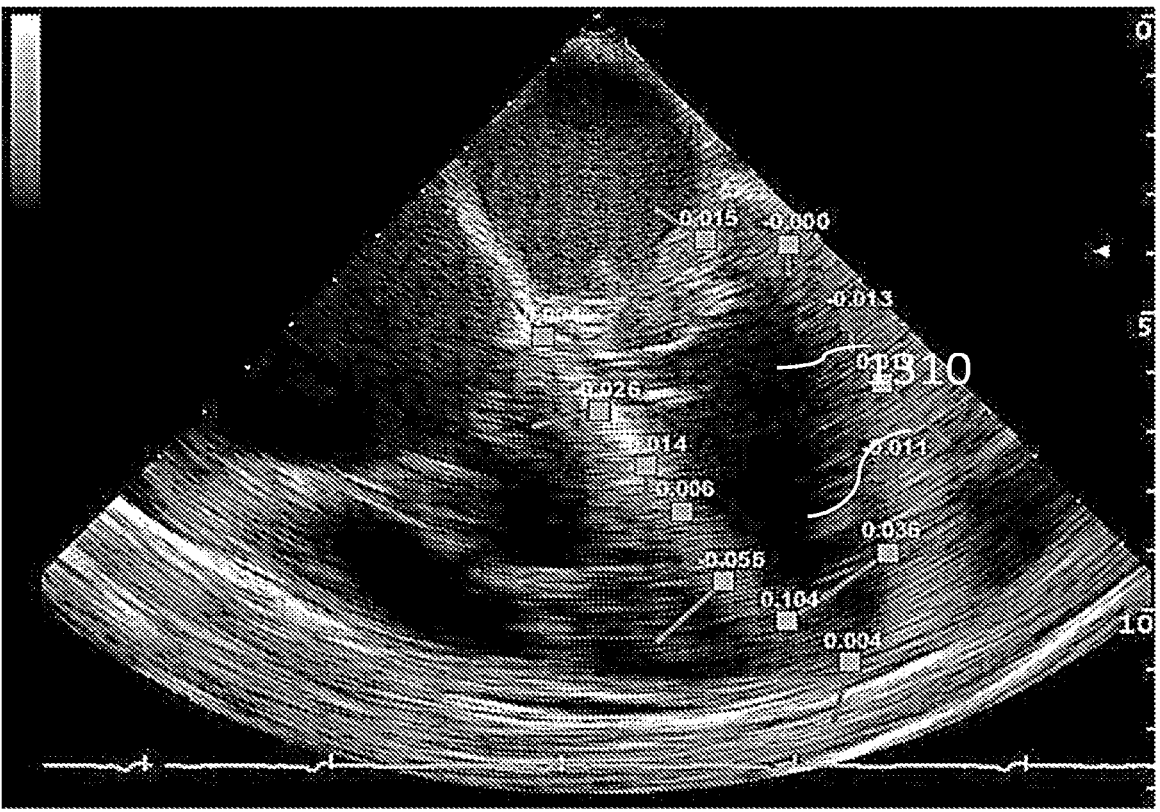

FIG. 13 shows the Strain vectors and their numerical values coded with color (dark grey boxes 1310 are colored red, and the rest of the boxes that are shown light gray can be green and state positive values).

Figure 14:
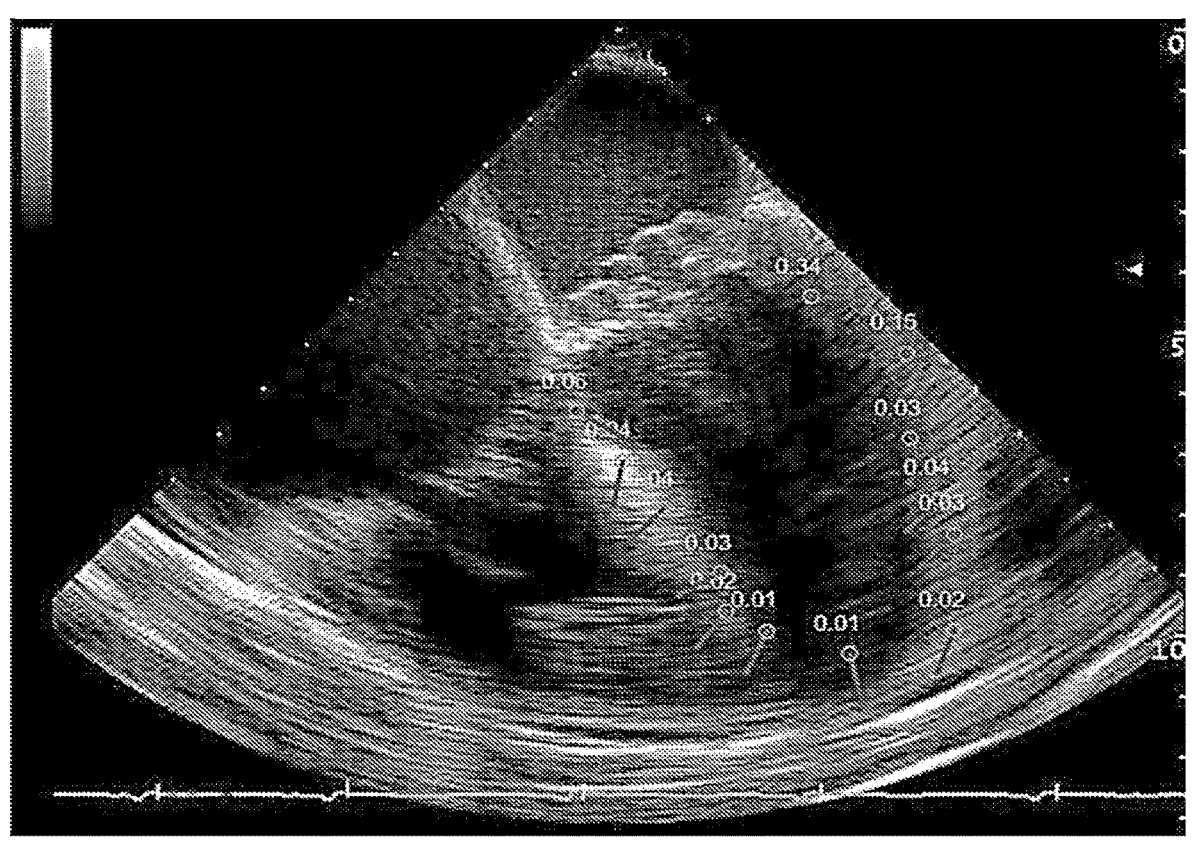

FIG. 14 shows the Force vectors and their numerical values (millimeter Newton).

Figure 15:
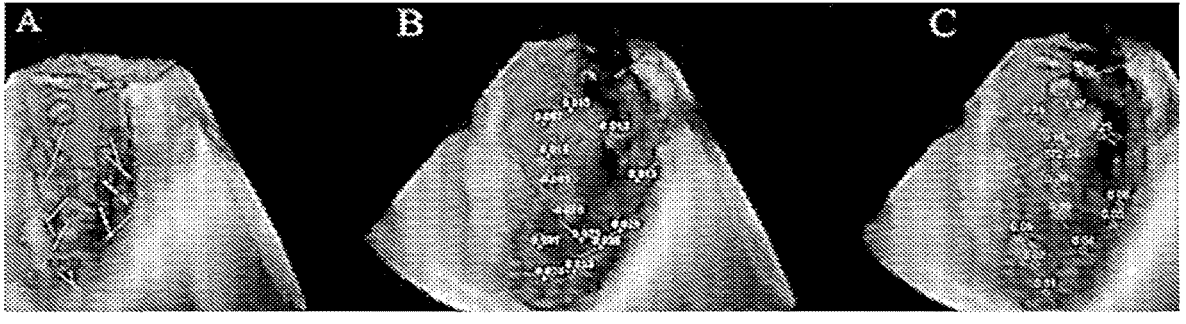

FIG. 15A-15C show the 3D Echocardiography images. FIG. 15A shows thirteen points selected in left in 3D left ventricle full volume and velocity vectors color codes and their numerical values attached to the selected points with mm/s unit. FIG. 15B shows thirteen points as selected; strain vectors are color coded with red (negative value) and green (positive value). FIG. 15C shows thirteen points selected and force vectors color coded with red color that result in those velocity and strain with their numerical values attached to the selected points with mmN (millimeter Newton) unit.

Figure 16:
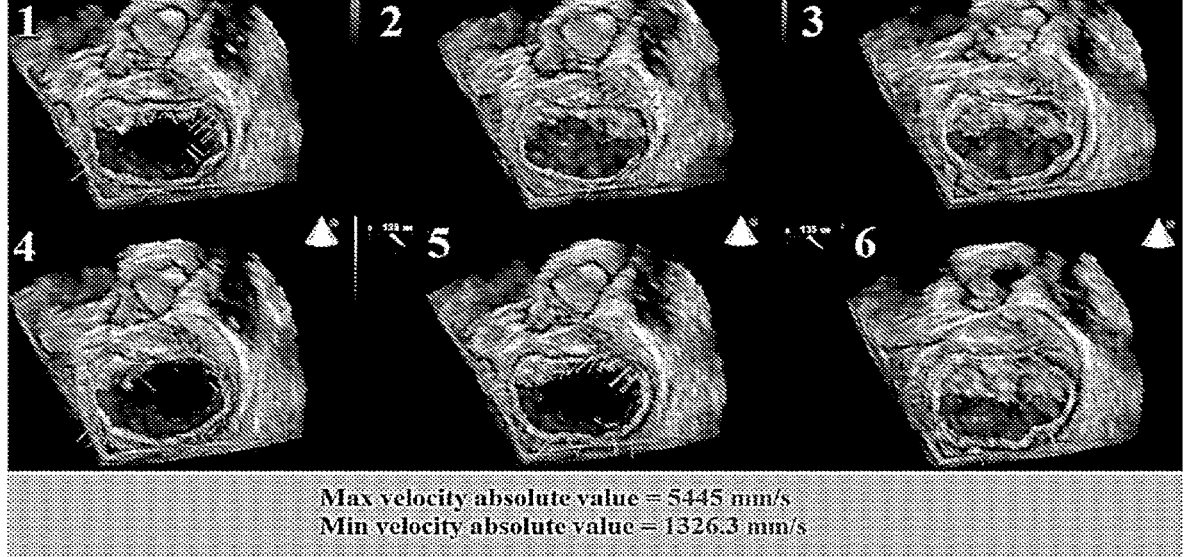

FIG. 16 shows mathematical imaging of mitral valve based on 3D TEE: the original number of volumes was twelve, which were increased to one twenty. In the six images, sixty points (red) were traced on the annulus of the mitral valve, and, similarly, selected sixty points on the mitral valve leaflets. The annulus and mitral valve leaflets were tracked by velocity vectors during the cardiac cycle. Different velocity vectors directions; shortening and lengthening are visible of each point in the annulus of the mitral valve. The absolute values of velocity were between 5445 mm/s and 1326.3 mm/s. Utilizing K-theory in algebraic geometry and the velocity vector fields of the mitral valve annulus and the mitral leaflets, can be distinguished with color the mitral valve annulus (blue), the posterior mitral valve leaflet (pink) and the anterior mitral valve leaflet (yellow) during the full cardiac cycle.

Figure 17:
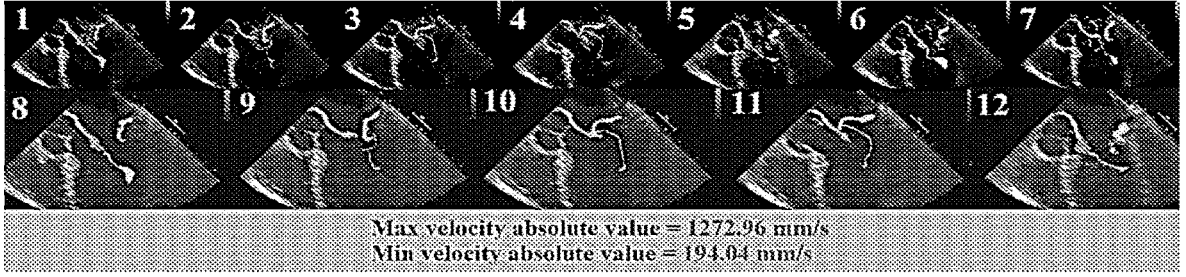

FIG. 17 shows the mathematical imaging of mitral valve apparatus based on 2D TEE: the sixty-six original frames was increased to six hundred sixty frames. Many pixels and phases were extracted within a cardiac cycle. In the images 1-7, one hundred twenty points (red) were traced on the mitral valve leaflets and behind the P2 prolapse in the left ventricular side. Different velocity vectors directions; shortening and lengthening are visible point by point. The absolute values of velocity were between 1272.96 mm/s and 194.04 mm/s.8-10). Using K-theory methods in the algebraic geometry, the anterior mitral valve leaflet (pink color), posterior mitral valve leaflet (green color), elongated chordae of a chordae of posterior leaflet (yellow) and chordae of the anterior mitral valve (white) could be tracked.

Figure 18:
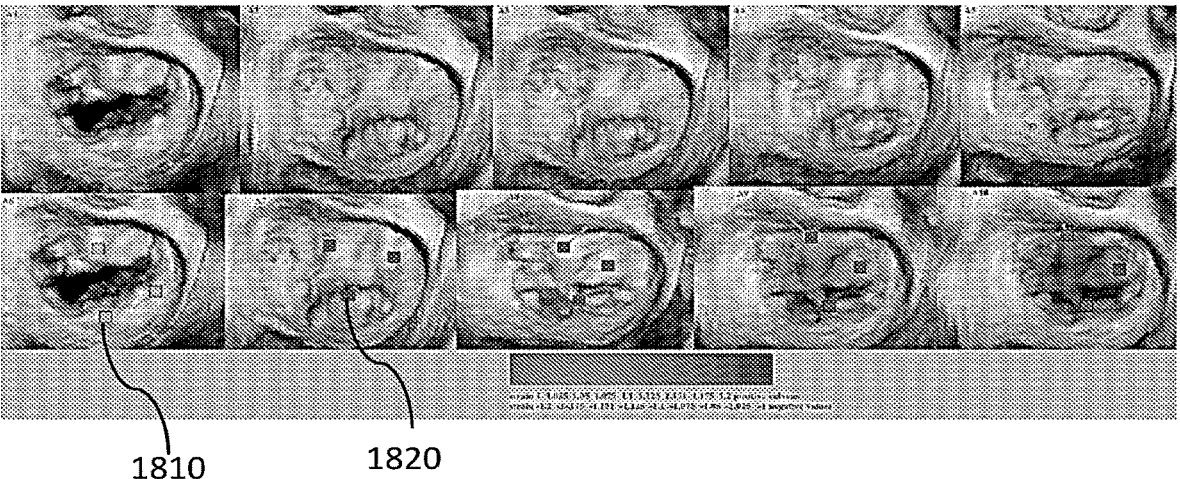

FIG. 18 illustrates the 3D voxel tracking and 3D strain computations for 3D image of the mitral valve. First row shows the Voxel tracking for five selected points; the second row shows the Color coding for 3D strain: red for negative values (shown by dark grey boxes 1820), green for positive values (shown by light grey boxes 1810). The colored spectrums change between green and red.

Figure 19:
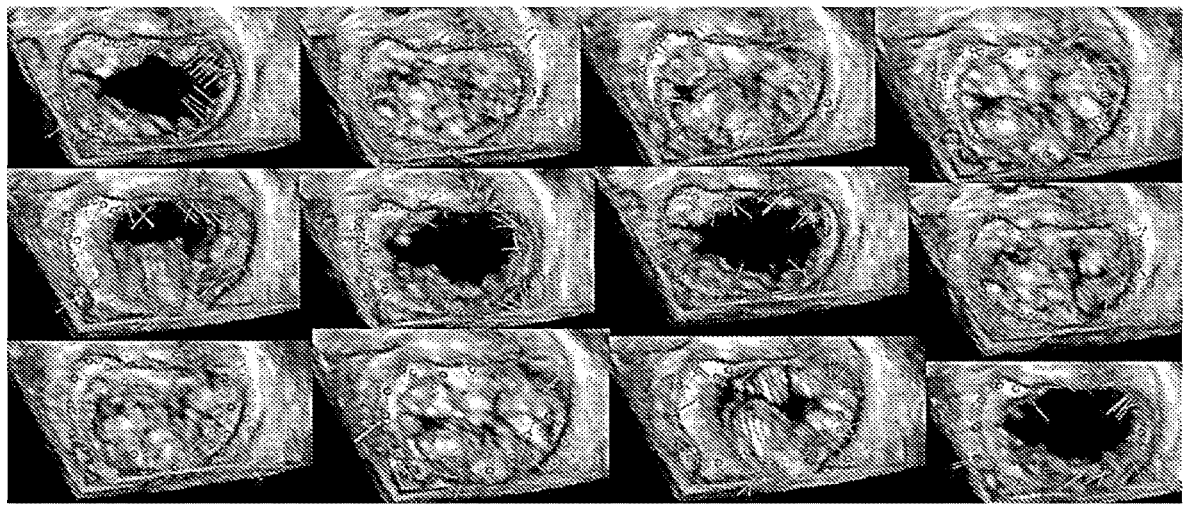

FIG. 19 shows the 3D mitral valve annulus structure and function mechanism in a MR case: about fifty points were traced on the annulus of the mitral valve. According to the increase in the volume, many hidden cardiac phases could be discovered. Consequently, the annulus visualizations were tracked by velocity arrows during the cardiac cycle. Different velocity vector directions and shortening and lengthening are visible point-by-point in the annulus of the mitral valve. This velocity vector filed attached to the mitral valve annulus, can help to realize the shape of the mitral valve annulus.

Figure 20:
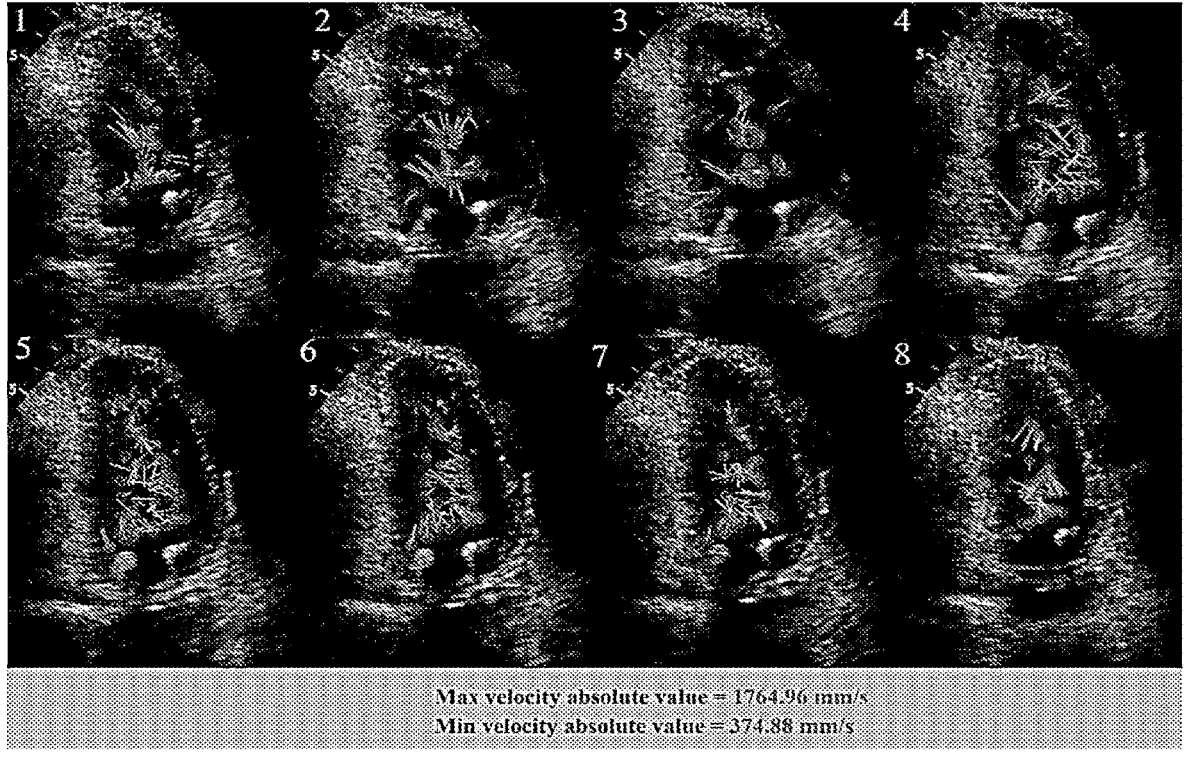

FIG. 20 shows normal blood velocity vectors overlaid on a sequence of 2D echocardiography apical long-axis views: LV intra-cavity blood flow velocity vectors during different phases per cardiac cycle are shown with sixty tracked red points in images (1-8). 1) the Blood fluid circulations in the rapid filling phase are non-rotational flow directions. 2) the Blood fluid moves rotationally in a clockwise directions at the diastasis phase, and 3) in the late filling phase that was characterized by a non-rotational flow obscuring the vortex. 4) in the early isovolumic contraction (IVC) period where the blood flow travels rotationally in a contour-clockwise direction. 5-7) the vortex was relocated in the proximity of the anterior mitral leaflet in the LVOT region are in contour-clockwise movements. 8) During the late IVC period and the end of systole, the vortex persisted in the left ventricular outflow tract region and directed flow towards aortic valve. The velocity absolute values were between 1764.96 mm/s and 374.88 mm/s.

Figure 21:
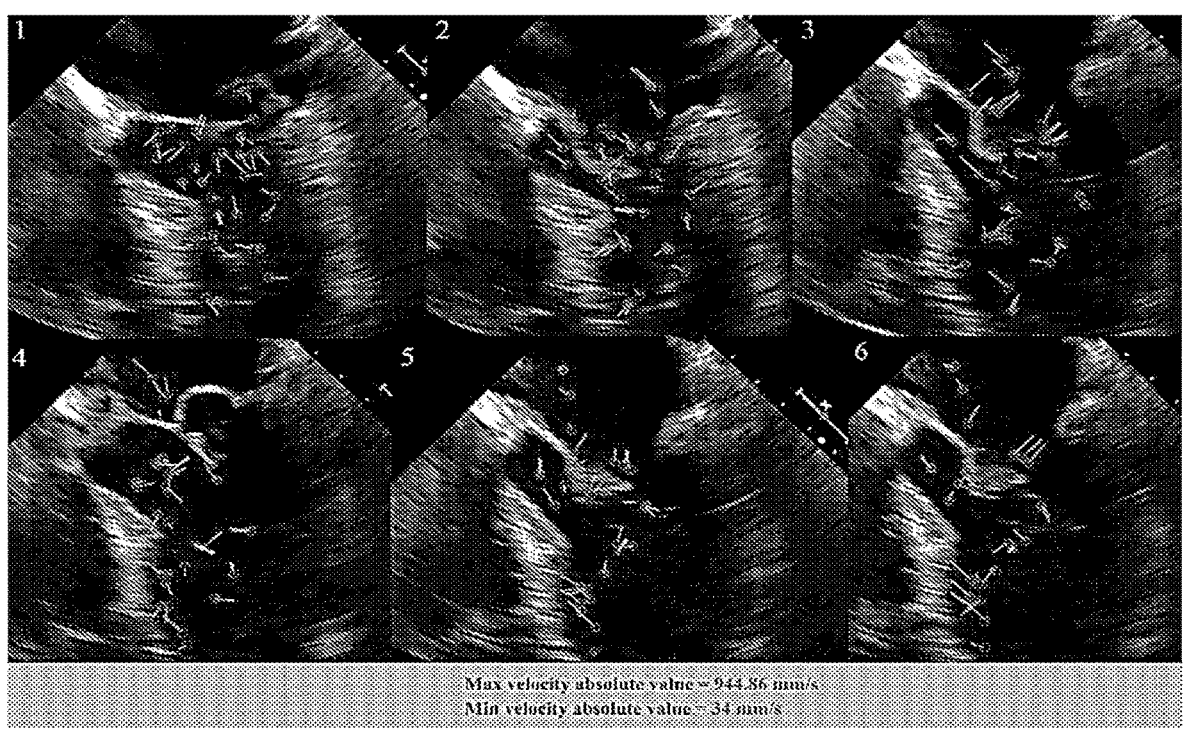

FIG. 21 shows examples of blood velocity vectors after a mitral valve P2 prolapse overlaid on a sequence of 2D echocardiography apical long-axis views: LV intra-cavity blood flow velocity vectors (green vectors) in a patient with a sever mitral valve regurgitation during different phases of cardiac cycle are shown with sixty tracked red points in (1-6). Normal blood flow develops along the longitudinal axis in association with the filling-emptying mechanism but here the base-apex function is replaced by disorganized dynamic actions. (1) During early systole, the blood velocity vectors rotate in clockwise directions behind the anterior mitral valve leaflet at the left ventricular side. (2) During the early opening of the mitral valve in rapid filling phase, blood velocity vectors were rotationally located in the base of the left ventricle around the mitral valve leaflets. (3) During the middle diastolic phase, the rotational blood velocity vectors were lengthened and shortened at the base and center of the left ventricle respectively. (4) During the end systole, the blood velocity vectors were directed eccentric anteriorly into the left atrium. (5) During the middle diastolic phase, the blood flow velocity vectors were turbulence in counterclockwise directions at the apical septum wall. (6) During the late atrial contraction phase, the blood velocity vectors were rotated in counterclockwise directions at the basal and apical segments respectively and also the velocity vectors were lengthened. The velocity absolute values were between 944.86 mm/s and 34 mm/s.

Figure 22:
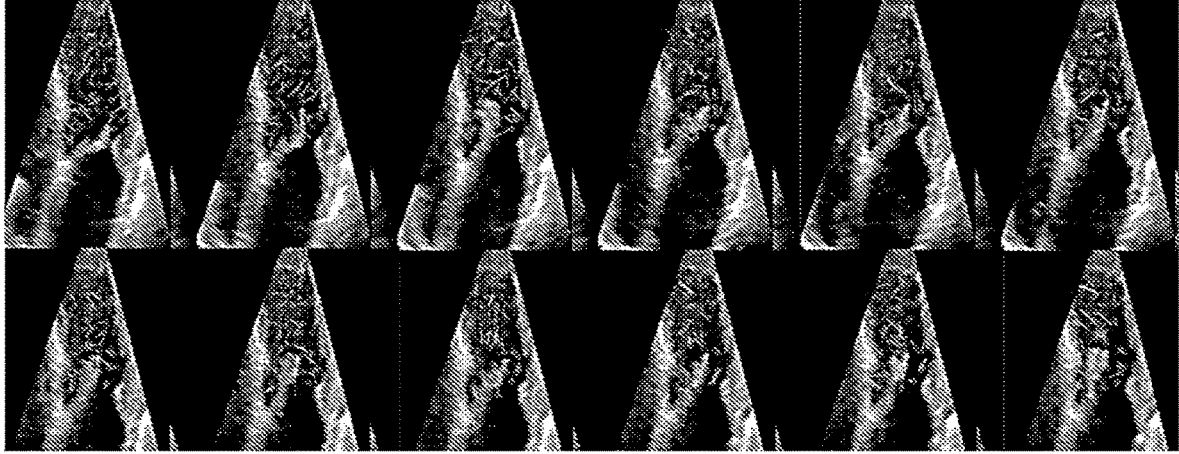

FIG. 22 shows a 3D mitral valve is represented by its 2D CONIC sections. Increasing the number of voxels and cardiac phases in different views per cardiac cycle: From left upper corner to the right lower corner. Examples of blood velocity vectors after a sever MR overlaid on a sequence of a 3D live LV volume in echocardiography apical long-axis views: (1-12) arrows indicate different vortex flow patterns during the opening and closing of the mitral valve in different cardiac phases.

Figure 23:
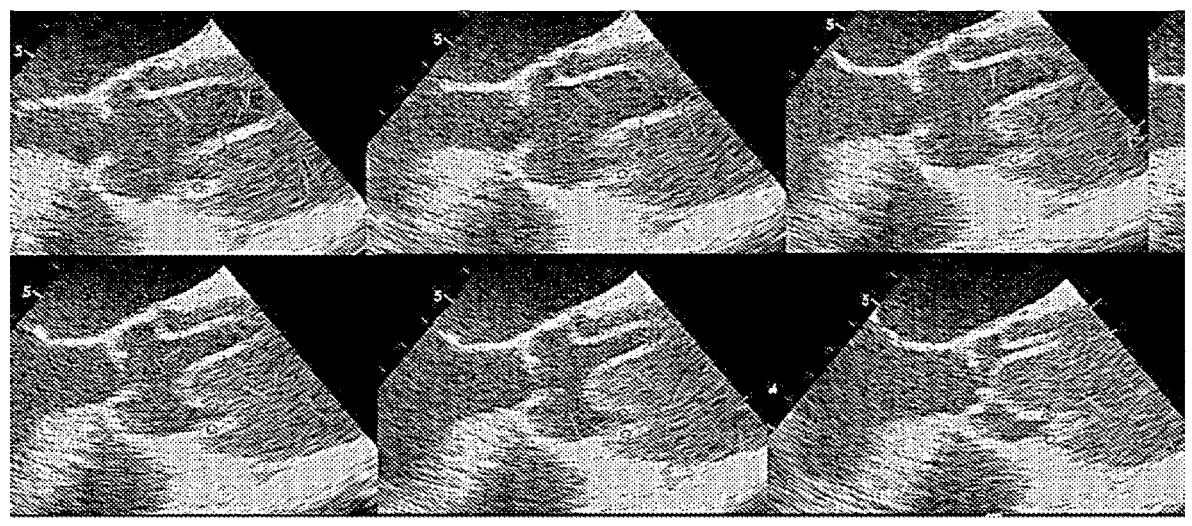

FIG. 23 shows a 2D Echocardiographic long-axis view of the blood fluid perturbation for a patient with aortic wall dissection. All quantitative indices like velocity, pressure etc. of the blood fluid are representable not only with different colored arrows but also with their numerical values. Here, the complexities of the blood fluid around the aortic wall dissection are easily visible.

Figure 24:
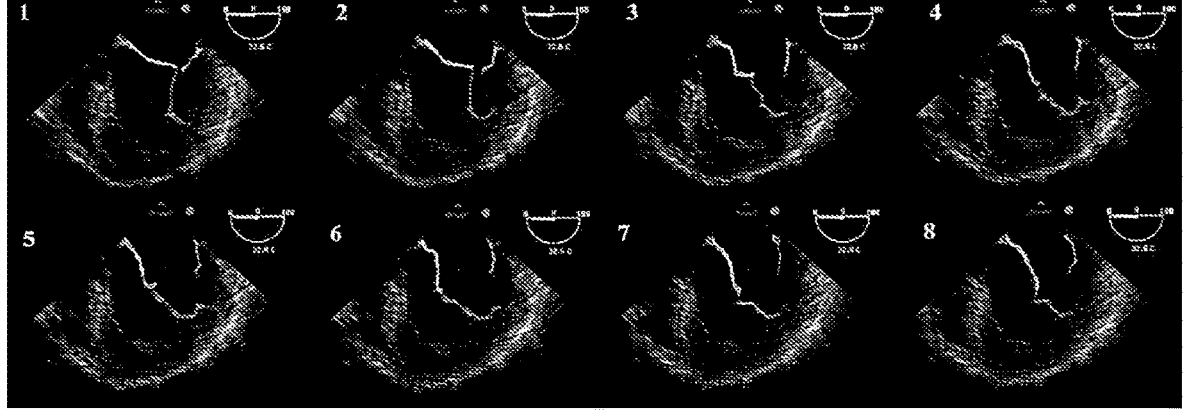

FIG. 24 shows a 2D mitral valve leaflet visualization: The number of fifty seven original frames were increased to five hundred seventy frames. A lot of pixels and phases were extracted within a cardiac cycle. 1-8) Using K-theory methods in algebraic geometry, anterior mitral valve leaflet curve can be tracked green color, posterior mitral valve leaflet curve with red color and a chordae curve with blue color. 4-5) by increasing the number of pixels, anterior papillary muscle and posterior papillary muscle were clearly found/observed.

Figure 25:
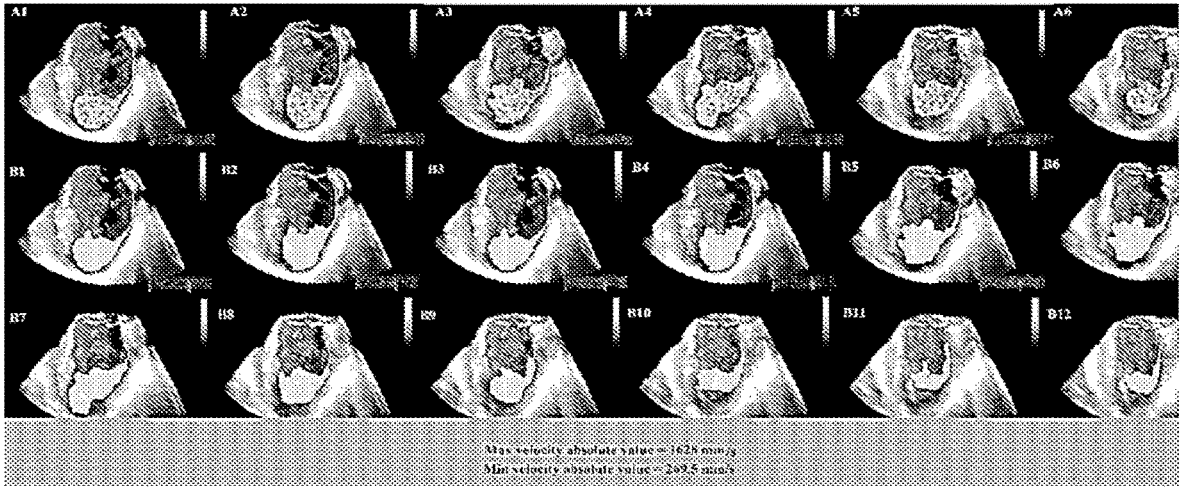

FIG. 25 show a 3D full left ventricular volume visualization: The number of fifty original volumes were increased to five hundred volumes. A lot of voxels and cardiac phases appeared. A1-A6) three arbitrary regions were selected. Sixty red points for each region were traced. Ninety thousand green velocity vectors were tracked/detected phase-by-phase per cardiac cycle. The velocity absolute values were between 1628 mm/s and 269.5 mm/s. (B1-B12) Using K-theory in algebraic geometry, these velocity vectors recovered three closed volumes in different regions with red (septal wall), yellow (apical wall) and blue (lateral wall) colors, respectively. Posterior mitral valve leaflet to green color and anterior mitral valve leaflet to pink color were clearly visualized.

Figure 26:
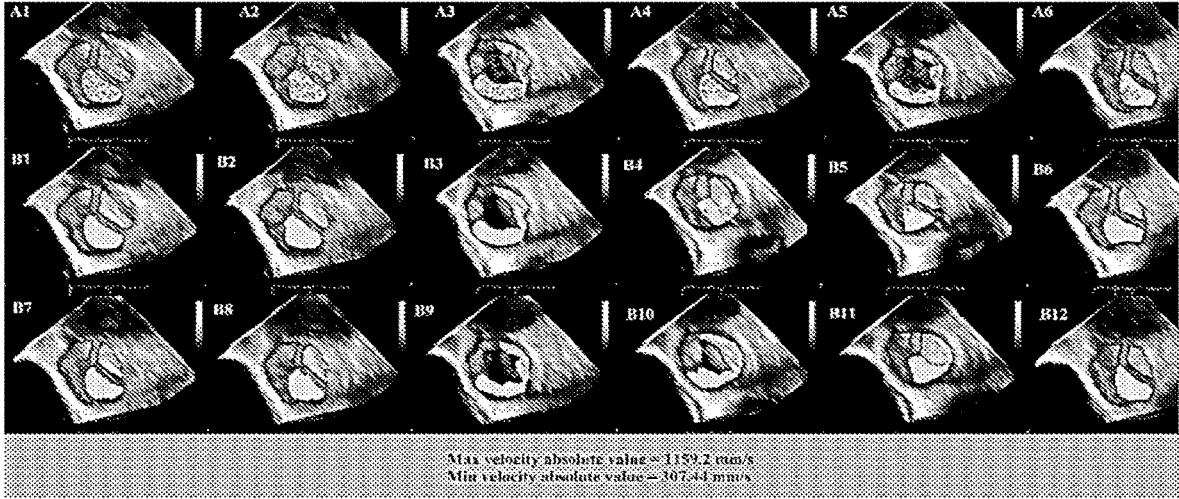

FIG. 26 shows 3D aortic valve cusps visualization: The number of eighteen original volumes were increased to 720 volumes. A lot of voxels and cardiac phases appeared. A1-A6) sixty red points for each cusp were traced. 1,29,600 green velocity vectors were tracked/detected phase by phase per cardiac cycle. The velocity absolute values were between 1159.2 mm/s and 307.44 mm/s. B1-B12) Using K-theory in algebraic geometry, these velocity vectors recovered three closed surfaces for each cusps with blue (left coronary cusp), yellow (non-coronary cusp) and green (right coronary cusp) colors, respectively. Opening and closing of the aortic valve cusps are easily visible and also one can see the LV cavity during the opening of the aortic valve.

Figure 27:
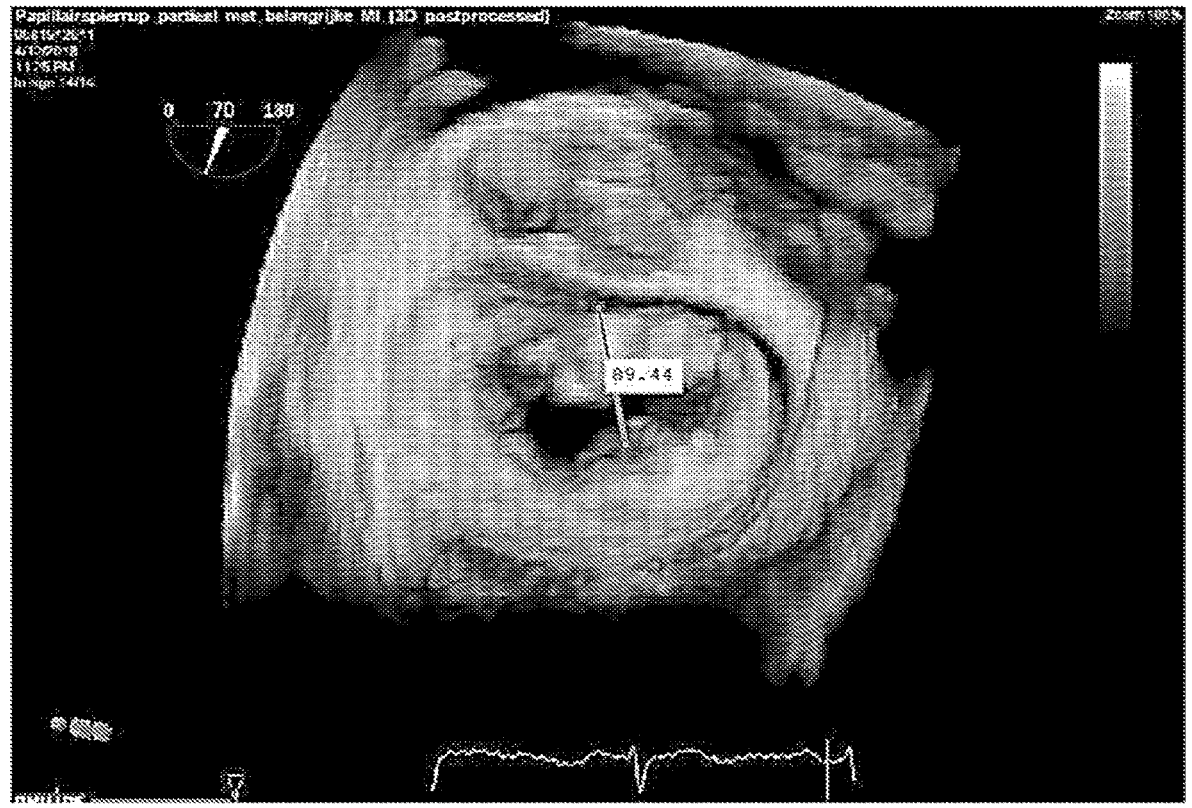

FIG. 27 shows 3d full volume based on 3d echo machines: the disclosed system uses a novel algorithm for these 3D reconstructions. The original case had fourteen volumes and in the system with ten times increasing to the one forty number of volumes: different sizes such as diameters, areas and volumes can be selected and then calculated automatically over the time in each heart phase.

Figure 28:
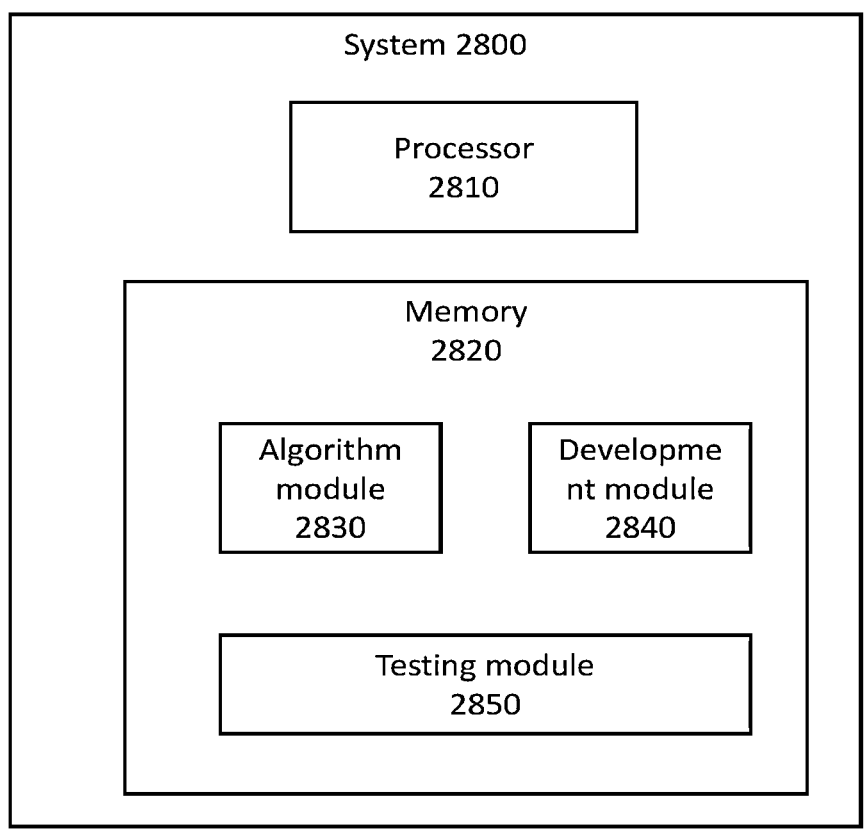

FIG. 28 shows the architecture of the disclosed system, according to an exemplary embodiment of the present invention.

Figure 29:
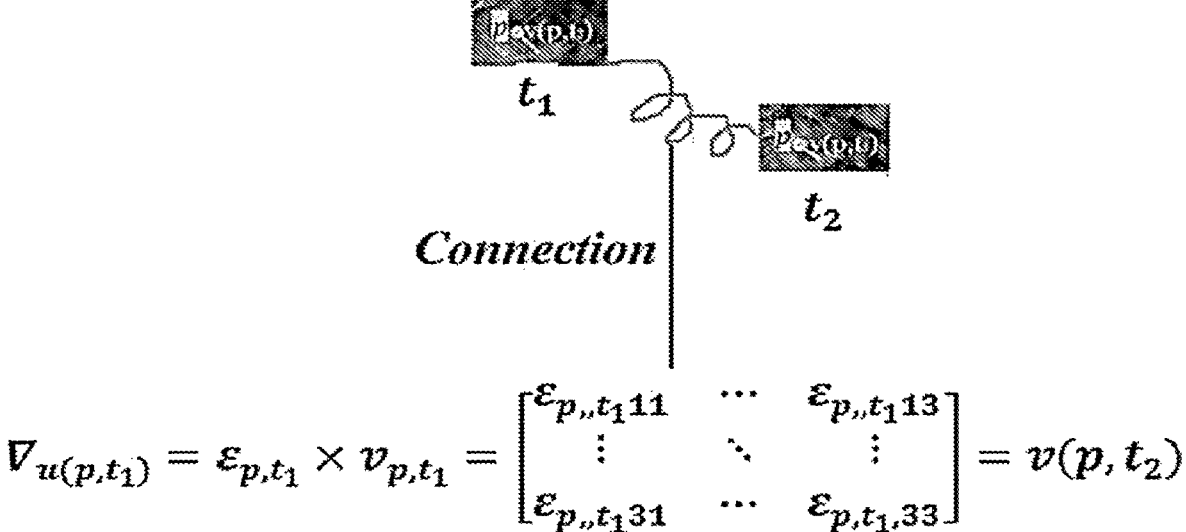

FIG. 29 shows for a cardiac segment 'p' during two different phases, vector 'v(p, $t_1$)' is connected to the vector 'v(p, $t_2$)' by the stent $\varepsilon_{p,t_1}$ after passing time $t_2$-$t_1$.

DETAILED DESCRIPTION

Subject matter will now be described more fully hereinafter. Subject matter may, however, be embodied in a variety of different forms and, therefore, covered or claimed subject matter is intended to be construed as not being limited to any exemplary embodiments set forth herein; exemplary embodiments are provided merely to be illustrative. Likewise, a reasonably broad scope for claimed or covered subject matter is intended. Among other things, for example, the subject matter may be embodied as apparatus and methods of use thereof. The following detailed description is, therefore, not intended to be taken in a limiting sense.

The word "exemplary" is used herein to mean "serving as an example, instance, or illustration." Any embodiment described herein as "exemplary" is not necessarily to be construed as preferred or advantageous over other embodiments. Likewise, the term "embodiments of the present invention" does not require that all embodiments of the invention include the discussed feature, advantage, or mode of operation.

The terminology used herein is to describe particular embodiments only and is not intended to be limiting to embodiments of the invention. As used herein, the singular forms "a", "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

The following detailed description includes the best currently contemplated mode or modes of carrying out exemplary embodiments of the invention. The description is not to be taken in a limiting sense but is made merely to illustrate the general principles of the invention since the scope of the invention will be best defined by the allowed claims of any resulting patent.

The following detailed description is described with reference to the drawings, wherein like reference numerals are used to refer to like elements throughout. In the following description, for purposes of explanation, specific details may be outlined in order to provide a thorough understanding of the subject innovation. It may be evident, however, that the claimed subject matter may be practiced without these specific details. In other instances, well-known structures and apparatus are shown in block diagram form in order to facilitate describing the subject innovation.

In one aspect, disclosed are a system and method for applying mathematical and physical laws to reversal wave data obtained from echo datasets to predict the trajectories of anatomical points in a cardiac cycle for heart modelling. The disclosed system allows to retrieve an infinite number of cardiac phases or volumes between the original cardiac phases and volumes, enabling the system to predict the coordinates of adjusting anatomical points and thereby increased spatial resolution even better than cardiac tomography (CT) systems. The system has three modules: the algorithm module, the development module, and the testing module based on real clinical cases.

In one aspect, the disclosed system and method uses 2D or 3D echo datasets stored in a DICOM file format. The disclosed system can extract 2D or 3D echo images or video clips from ultrasound reversal waves of the 2D or 3D echo datasets. The disclosed system can then assign and track an arbitrary pixel or voxel on the extracted images per cardiac cycle (phase by phase). Thereafter the system can determine an original reversal wave equation $\rho_p$ attached to the arbitrary pixel or voxel p. Thereafter, the system, using Lagrange-Euler equations, extracts the curve with passed from the selected pixel or voxel p within a cardiac cycle. The Lagrange-Euler equations are reformulated based on 2D and 3D echo data sets, which is called "$f_p$" deformable map. The system can then generate reconstructed curvelets from the interior products $\rho_p$ and $f_p$ that is called by $c_p = \rho_p \cdot f_p$; wherein the $c_p$'s are new coefficients for the new 2D and 3D curvelets attached p. From the new coefficients, 2D and 3D images or frames are reconstructed. The new 2D/3D video clips are made vs. the original 2D/3D echo video clips. 2D and 3D pixel/voxel tracking program are coded and run per a cardiac cycle. New 2D and 3D quantitative data like motion (velocity and displacement of a voxel) and Deformation (longitudinal, radial, and circumferential strain component for each voxel) can then be calculated. A geometrical important index which is called "Curvature" is reformulated based on 3D echo datasets and then coded as distinct colors on the full volume for example whenever the curvature is positive, it can be coded as green color and so on.

In one aspect, any above structures can be distinguished with separate colors and can be tracked throughout the cardiac cycle, like mitral annulus, valve leaflets and chordae.

In one aspect, disclosed is an ultra-resolution mathematical 2D and 3D echocardiographic platform. Ultrasound is the most widely used imaging modality in medicine and especially in cardiovascular patients for diagnosis, treatment, follow-up, and guided interventions. The disclosed system and method can overcome the fundamental limitations with Ultrasound imaging modality i.e., low 3D volumes (coupled with moving intra-cardiac structures) and inability to capture all the mechanical events in the heart.

In one aspect, disclosed is an imaging platform based on physical laws, mathematics, and numerical algorithms on reversal wave data to retrieve the trajectories of all the anatomical points and retrieve infinite number of frames or volumes from the original dataset. The disclosed system and method, by converting the image data into mathematical data/pixel data, can provide a precise temporal vector tracking of any landmark position with precise in-plane mechanical properties including vector velocity and strain without needing a Doppler.

In one aspect, the disclosed platform can be universal and can process the input of any echocardiographic imaging platform and can in theory be built in any system for live-processing or be coupled with other techniques. In clinical settings, the frame rate could be increased for 2D echo to 1000 frames (compared to current clinical maximum around 50-60 frames/s) and for 3D to 500 volumes/s (compared to current clinical maximum around 35-40 volumes/s).

In one aspect, the disclosed system and method can be applied to other imaging modalities, such as CT/MRI. The disclosed system and method may also provide for development of ultra-resolution image fusion and simulation. For example, image fusion of CT-scan and ultrasound. The disclosed platform, by converting image data into mathematical data of both CT and ultrasound, and creating new equations, can provide for creating new imaging fusion modality. The principles of artificial intelligence can be incorporated without departing from the scope of the present invention. It is also envisioned that the disclosed system and method can provide for fusion of auto quantitative indices (like motional and deformational indices) to images.

Disclosed are a system and method for medical imaging-based modeling of a heart for therapeutic and diagnostic applications. The disclosed system and method can use existing data from an imaging modality, such as echocardiography data to create a virtual heart model with high resolution and depicting all the movements in the heart.

Figure 1:
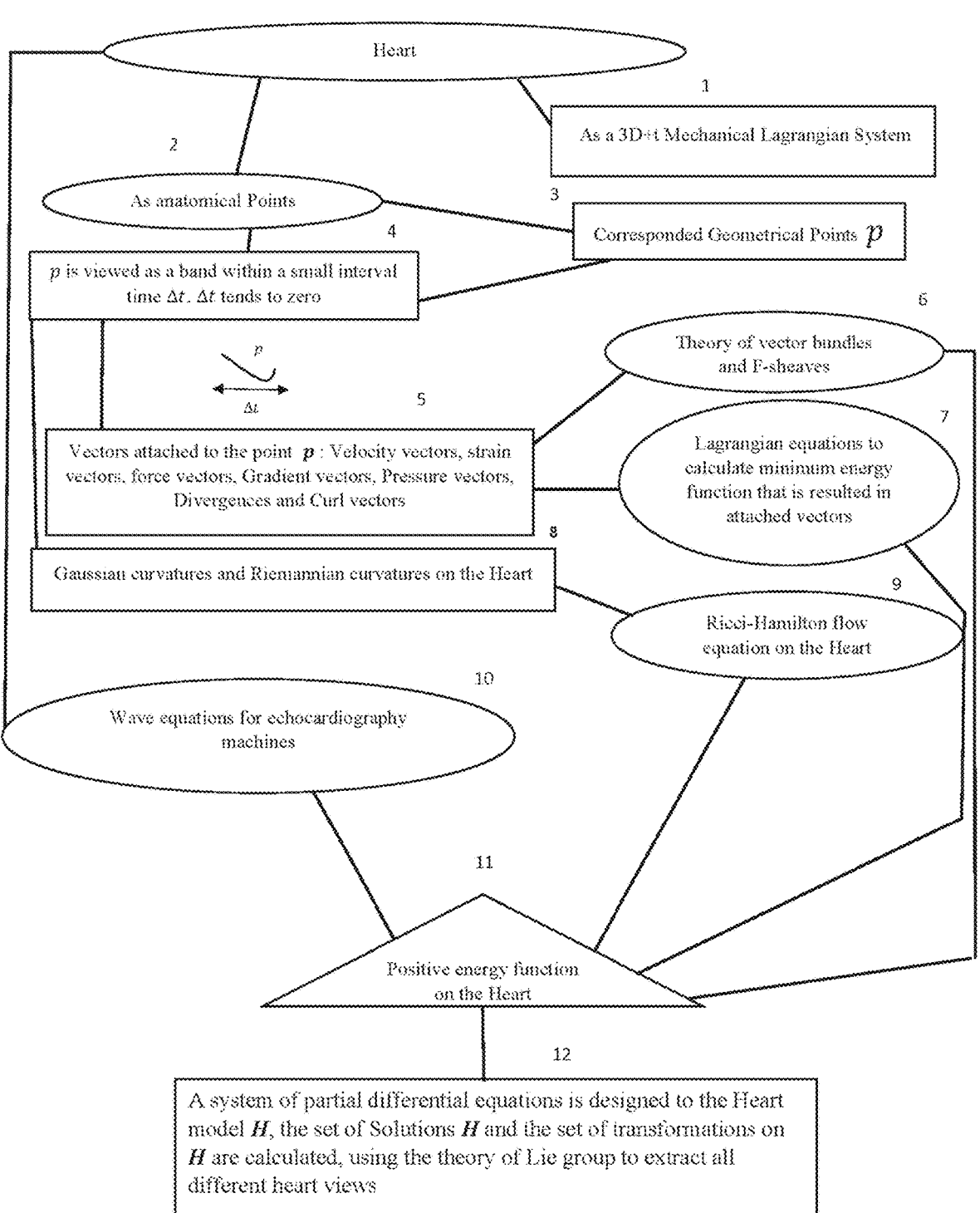
FIG. 1 is a block diagram illustrating the disclosed method for human heart modelling, according to an exemplary embodiment of the present invention.
Figure 1A:
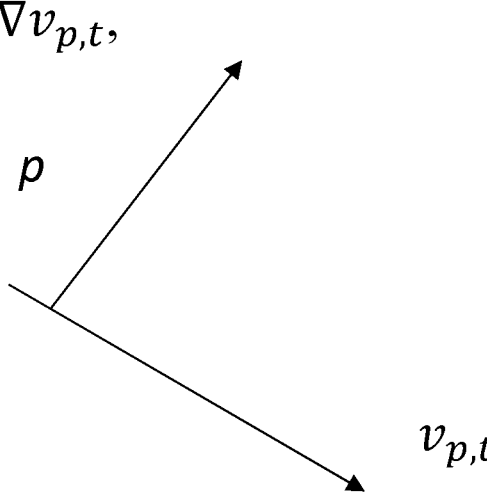
FIG. 1A is a diagram showing a cardiac point p at the phase t with the velocity vector $v_{p,t}$.

Referring to FIG. 1, the disclosed system and method assumes the heart mathematically as a 3D+t=4D manifold based on the Lagrangian mechanical system 1, as a biological circulatory system corresponds to a 4D manifold in space and time. Anatomical points ('p') 2 correspond to the geometrical points of a 3D+t=4D smooth manifold H 3. Each geometrical point moves in a closed time interval during cardiac cycle 4. Velocity vector fields are considered phase by phase resulting in a bundle of velocity vectors $v_{p,t}$, shown in FIG. 1a.

A cardiac point p at the phase t with the velocity vector $v_{p,t}$ and gradient vector $\nabla v_{p,t}$, $V_t$ is the space of velocity vectors attached at time t 5. Based on the F-sheaves theory 6, to have the space of "3 by 3" matrices thorough the time in a cardiac cycle as follow:

$$H_p(t) :=$$

$$\begin{array}{cccc}
v_{p,t} & v_{p,t,x} & v_{p,t,y} & v_{p,t,z} \\
(v_{p,t} \cdot \nabla v_{p,t})v_{p,t} = & \frac{\partial v_{p,t,x}}{\partial x}v_{p,t,x} & \frac{\partial v_{p,t,y}}{\partial y}v_{p,t,y} & \frac{\partial v_{p,t,z}}{\partial z}v_{p,t,z} \\
(v_{p,t} \times \nabla v_{p,t})v_{p,t} & \frac{\partial v_{p,t,y}}{\partial y}-\frac{\partial v_{p,t,x}}{\partial x} & \frac{\partial v_{p,t,z}}{\partial z}-\frac{\partial v_{p,t,x}}{\partial x} & \frac{\partial v_{p,t,y}}{\partial y}-\frac{\partial v_{p,t,z}}{\partial z}
\end{array}$$

The first row describes the velocity components, the second row shows the divergence at the point p and the third row states the vortices at the point p phase by phase within a cardiac cycle. Therefore, H is realized as a stack of smooth 3D manifolds (cross sections of H) through the cardiac cycle toward the velocity vector fields.

The 3D strains are presented by 3 by 3 matrices in the following way:

$$\varepsilon_{p,t} = \begin{bmatrix} \varepsilon_{p,t,11} & \cdots & \varepsilon_{p,t,13} \\ \vdots & \ddots & \vdots \\ \varepsilon_{p,t,31} & \cdots & \varepsilon_{p,t,33} \end{bmatrix}$$

Force indices are formulated and calculated based on extracted motion and deformation parameters by the following tensor product:

$$F_{p,t} = H_p(t) \otimes \varepsilon_{p,t}$$

$$= \begin{array}{ccc} v_{p,t,x} & v_{p,t,y} & v_{p,t,z} \\ \frac{\partial v_{p,t,x}}{\partial x}v_{p,t,x} & \frac{\partial v_{p,t,y}}{\partial y}v_{p,t,y} & \frac{\partial v_{p,t,z}}{\partial z}v_{p,t,z} \\ \frac{\partial v_{p,t,y}}{\partial y}-\frac{\partial v_{p,t,x}}{\partial x} & \frac{\partial v_{p,t,z}}{\partial z}-\frac{\partial v_{p,t,x}}{\partial x} & \frac{\partial v_{p,t,y}}{\partial y}-\frac{\partial v_{p,t,z}}{\partial z} \end{array} \otimes$$

$$\begin{bmatrix} \varepsilon_{p,t,11} & \cdots & \varepsilon_{p,t,13} \\ \vdots & \ddots & \vdots \\ \varepsilon_{p,t,31} & \cdots & \varepsilon_{p,t,33} \end{bmatrix}$$

General force of p per cardiac cycle is the summation of the above formula:

$$F_P = \bigoplus_{t \text{ runs in a cardiac cycle}} F_{p,t}$$

$$= \bigoplus_{t \text{ runs in a cardiac cycle}} \bigotimes$$

$$\begin{array}{ccc}
v_{p,t,x} & v_{p,t,y} & v_{p,t,z} \\[4pt]
\dfrac{\partial v_{p,t,x}}{\partial x} v_{p,t,x} & \dfrac{\partial v_{p,t,y}}{\partial y} v_{p,t,y} & \dfrac{\partial v_{p,t,z}}{\partial z} v_{p,t,z} \\[8pt]
\dfrac{\partial v_{p,t,y}}{\partial y} - \dfrac{\partial v_{p,t,x}}{\partial x} & \dfrac{\partial v_{p,t,z}}{\partial z} - \dfrac{\partial v_{p,t,x}}{\partial x} & \dfrac{\partial v_{p,t,y}}{\partial y} - \dfrac{\partial v_{p,t,z}}{\partial z}
\end{array}$$

$$\begin{bmatrix} \varepsilon_{p,t,11} & \cdots & \varepsilon_{p,t,13} \\ \vdots & \ddots & \vdots \\ \varepsilon_{p,t,31} & \cdots & \varepsilon_{p,t,33} \end{bmatrix}$$

The Lagrangian equation for 3D cardiac segment (point p) is described by the following reformulation based on the acquired datasets:

$$L(p, \dot{p}, \varepsilon_P, \dot{\varepsilon}_P, t) = T(p, \dot{p}, \varepsilon_{P,t}, \dot{\varepsilon}_{P,t}) - U(p, \dot{p}, \varepsilon_{P,t}, \dot{\varepsilon}_P, t)$$

$$= \frac{1}{2}\rho[\delta \text{Volume}_{p,n}(t_n) + p_1 p_2 p_3]\dot{p}^2 - \frac{1}{2}$$

$$\left( \sum_{\ell_{p,r} \in \ell_p^*} \left( \sum_{1 \le i,j \le 3} \varepsilon_{p,t,ij,\ell_p} \cdot p_i \cdot p_j \right) \right) p^2$$

Where: $\ell_p^*$ is the set of all fibers passing through p; $\delta \text{Volume}_p(t)$ is the change in volume of the point p from the first volume to n's volume in time $t_n$; and $\delta \text{Volume}_{p,n}(t_n)$ is the determinant of strain matrix:

$$\varepsilon_{p,t} = \begin{bmatrix} \varepsilon_{p,t,11} & \cdots & \varepsilon_{p,t,13} \\ \vdots & \ddots & \vdots \\ \varepsilon_{p,t,31} & \cdots & \varepsilon_{p,t,33} \end{bmatrix}$$

Based on this, Lagrangian equations are reformulated:

$$\frac{\partial L(p, \dot{p}, \varepsilon_{P,t}, \dot{\varepsilon}_P, t)}{\partial p} - \frac{d}{dt}\left( \frac{\partial L(p, \dot{p}, \varepsilon_{P,t}, \dot{\varepsilon}_p, t)}{\partial \dot{p}} \right) =$$

$$F_P = \bigoplus_{t \text{ runs in a cardiac cycle}} F_{p,t}$$

$$= \bigoplus_{t \text{ runs in a cardiac cycle}}$$

$$\begin{array}{ccc}
v_{p,t,x} & v_{p,t,y} & v_{p,t,z} \\[4pt]
\dfrac{\partial v_{p,t,x}}{\partial x} v_{p,t,x} & \dfrac{\partial v_{p,t,y}}{\partial y} v_{p,t,y} & \dfrac{\partial v_{p,t,z}}{\partial z} v_{p,t,z} \\[8pt]
\dfrac{\partial v_{p,t,y}}{\partial y} - \dfrac{\partial v_{p,t,x}}{\partial x} & \dfrac{\partial v_{p,t,z}}{\partial z} - \dfrac{\partial v_{p,t,x}}{\partial x} & \dfrac{\partial v_{p,t,y}}{\partial y} - \dfrac{\partial v_{p,t,z}}{\partial z}
\end{array} \otimes \begin{bmatrix} \varepsilon_{p,t,11} & \cdots & \varepsilon_{p,t,13} \\ \vdots & \ddots & \vdots \\ \varepsilon_{p,t,31} & \cdots & \varepsilon_{p,t,33} \end{bmatrix}$$

By implementing these equations, can be provided curves $l_P$'s point by point. In fact, a fibre bundle of curves $l_P$'s can be constructed. This fibre bundle represents flow movements (optimized trajectories) of each cardiac point per cardiac cycle.

Addition of Gaussian curvatures, connections, Riemannian curvatures, and Hamilton-Ricci flow equation:

For a cardiac point 'p' was obtained the optimized trajectory $l_P$. Was set the Gaussian curvature 8 point 'p' along the optimized trajectory $l_P$ by the following formula:

$r_{l_p}$=The Gaussian curvature at the point 'p'

$$\tan \alpha_{l_p} = \|\dot{l}_P\| \to \to \alpha_{l_p} = \arctan(\|\dot{l}_P\|)$$

$$r_{l_p} = \int_{p \text{ runs away on the cardiac points}}^{p \text{ runs away on the cardiac points}} \alpha_{l_p} = \arctan(\|\dot{l}_P\|)$$

H as a 4D smooth manifold is divided to $H_3$ and $H_2$. $H_1$ is constructed based on Lagrangian equations and $H_2$ is constructed by utilizing Hamilton-Ricci flow equations 9.

Whenever a cardiac point 'p' moves along the optimized trajectory $l_P$ for instance from phase $t_1$ with the velocity vector $v(p, t_1)$ and stain $\varepsilon_{p,t_1}$ to next the phase $t_2$ with the velocity vector 'v(p, $t_2$)'. Vectors 'v(p, $t_1$)' and 'v(p, $t_2$)' connect by something like a stent (FIG. 29). This connection is defined by the following manner:

$$\nabla_{v(p,t_1)} = \varepsilon_{p,t_1} \times v_{p,t_1} = \begin{bmatrix} \varepsilon_{p,t_1 11} & \cdots & \varepsilon_{p,t_1 13} \\ \vdots & \ddots & \vdots \\ \varepsilon_{p,t_1 31} & \cdots & \varepsilon_{p,t_1 33} \end{bmatrix} = v(p, t_2)$$

On the other hands, vector 'v(p, $t_1$)' is connected to the vector 'v(p, $t_2$)' by the stent $\varepsilon_{p,t_1}$ after passing time $t_2$-$t_1$ in a manner, as shown in FIG. 29, shows for a cardiac segment 'p' during two different phases, vector 'v(p, $t_1$)' is connected to the vector 'v(p, $t_2$)' by the stent $\varepsilon_{p,t_1}$ after passing time $t_2$-$t_1$. The system provides these connections phase by phase per cardiac cycle. Therefore, the Riemannian curvature 'g' can be reformulated by the following way:

$$g(u,v)(w) = \nabla_u \nabla_v w - \nabla_v \nabla_u w$$

The Hamilton-Ricci flow equations $$\frac{dg}{dt} = (r - R)g$$

state the bending behavior of Heart (H) where r is the whole Gaussian curvature and R is the average of $r_{l_p}$'s. Finally, based on the echocardiography, a set of partial differential equations (PDEs) were designed 10-12 based on all obtained equations, to construct a mathematical heart model H. The set of solutions H of these PDEs were calculated numerically using spectral methods. The set of all transformations on H was extracted based on Lie theory. By this disclosed model, the system can extract from patient-specific images, real-time in-plane mechanical parameters from any anatomic points that will form the basis for patient-specific heart modelling.

Referring to FIG. 2, FIG. 3, FIG. 4, FIG. 5 and FIG. 6:

Echocardiographic datasets can be acquired from any echocardiography machines like Philips (EPIQ CVx and iE33 xMATRIX), GE Healthcare (Vivid 3, Vivid 7 and LOGIQ E9) and Esaote (MyLab™ 60, MyLab™ 70). Original reversal equation waves are extracted for each anatomical point. The wave equations are partial differential equations, which are scalar functions $w = w(x_1, x_2, t)$ of a time variable t and spatial variable $x_1, x_2$. The magnitude w is the displacement of vibrant cardiac segments away from their resting locations from end of systole to the end of diastole in one cardiac cycle. The equations are:

$$\frac{\partial^2 w}{\partial t^2} = c^2 \left( \frac{\partial^2 w}{\partial x_1^2} + \frac{\partial^2 w}{\partial x_2^2} \right)$$

Wave equations are solved for each echocardiographic segment as linear combinations of simple solutions that are sinusoidal plane waves with various directions of propagation and wavelengths, but all with the same propagation speed c. By applying Fourier transform to the wave solution, can be obtained velocities of anatomical points in original phases per cardiac cycle. Therefore, the strain components and myocardial torsions can be quantified. Longitudinal strain (shortening and lengthening), radial strain (thickening) and torsion indices are extracted for each segment within the heart cycle by the formula below.

Original echocardiographic segments are acquired. These segments are mapped to the Cartesian plane as geometrical points. Was searched the regions of p's point at time $t_n$ corresponding to n's frame and were labeled $d_n$. If $J_{n,t_n}$ are distances between i's point at first frame and $d_n$ corresponding to time $t_n$, strain value of the pth point at time $t_n$ is:

$$\varepsilon(p, t_n) = \sum_{k=1}^{n-1} (J_{k+1,t_{k+1}}, - J_{k,t_k})/J_{k,t_k}$$

Velocity vectors are stretched as the calculated strain values. Therefore, motion and deformation are considered simultaneously.

Hadamard transform for fast running and high intensity resolution was used. K-theory in algebraic geometry was used to distinguish structures during the entire cardiac cycle by use of colors. Clinical verification tests were applied on echocardiographic datasets for different echocardiography machines. C++ coding for 3D cases to read original files and write new datasets is based on defining many commands to create 4D mathematical matrices attached to 3D cases.

Figures 2A, 2B:
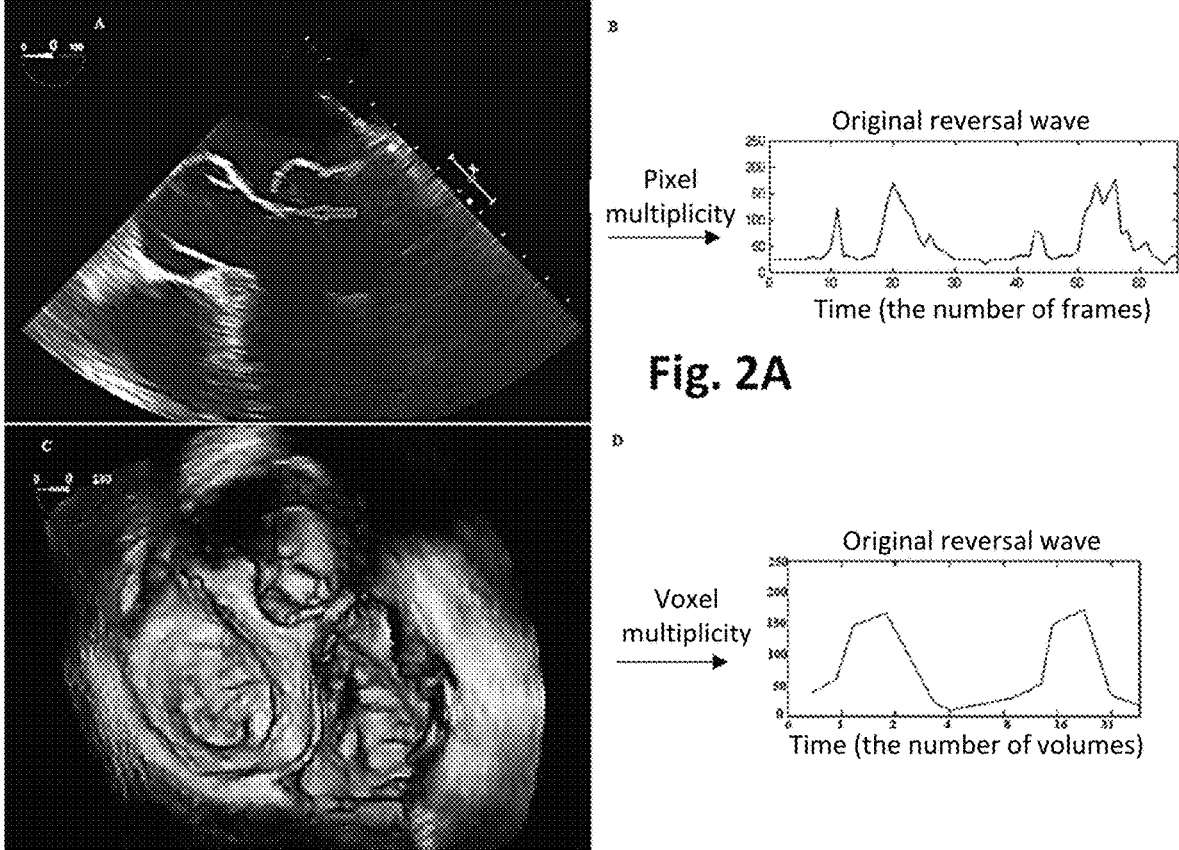
FIG. 2A illustrates 2D DICOM file showing a 2D long-axis view of a mitral valve and its conversion to a 2D reversal wave over time, vertical axis shows pixel multiplicity and horizontal axis shows the number of original cardiac phases, according to an exemplary embodiment of the present invention.
FIG. 2B shows a 3D DICOM file conversion to 3D reversal wave over time, the 3D DICOM file shows a 3D view of the aortic, mitral, and tricuspid valves, vertical axis in the 3D reversal waves over time shows pixel multiplicity and the horizontal axis shows the number of original cardiac phases, according to an exemplary embodiment of the present invention.

Development of mathematical algorithms for 2D datasets:

STEP 1: A 2D image is formed by pixels, so the first step is to extract the coordinates of the original pixel positions in time and space from reversal waves and equations. For example, when using echocardiographic images based on the 2D original ultrasound reversal waves and Fourier coefficients, it is possible to extract the original cardiac segment position in space and time for each corresponding point within a cardiac cycle (FIGS. 2; 2A and 2B).

STEP 2: The second step is to extract and calculate mechanical parameters, such as motion and deformation indices, of the original pixels. This allows the formulation and calculation of force indices. The force formula based on velocity, displacement, strain, and strain rate is:

$$f(p, n, d_n(p), v(p, n, t), \varepsilon(p, n, t_n), \varepsilon'(p, n, t_n), t_n) =$$
$$\frac{2d_n(p)}{t_n^2} + 2\varepsilon'(p, n, t_n) \cdot \left[\frac{\varepsilon(p, n, t_n) + 1)d_0(p)}{t_n}\right] - \frac{2v(p, n, t)}{t_n} \quad (1)$$

Wherein, p is a 2D cardiac segment; $d_n(p)$ is the displacement of p at n's frame; $v(p, n, t)$ is velocity at the same frame; and $\varepsilon(p, n, t_n)$, and $\varepsilon'(p, n, t_n)$ are the strain and strain rate at n's frame. The general force of p per cardiac cycle is the summation of the formula (1).

STEP 3: The third step is to find the cardiac segment (pixel) trajectory based on Lagrangian equations. It is important to reformulate this system of equations based on echocardiographic datasets. Lagrangian equations for a 2D cardiac segment (point p) are described by the following reformulation based on acquired datasets:

$$L(p, \dot{p}, \varepsilon_P, \dot{\varepsilon}_P, t) = \quad (2)$$
$$T(p, \dot{p}, \varepsilon_P, \dot{\varepsilon}_{P,t}) - U(p, \dot{p}, \varepsilon_P, \dot{\varepsilon}_P, t) = \frac{1}{2}\rho[\delta A_{p,n}(t_n) + p_1 p_2]\dot{p}^2 -$$
$$\frac{1}{2}\left(\sum_{\ell_{p,r} \in \ell_p} * \left(\sum_{1 \leq i,j \leq 2} \varepsilon_{p,i,j,\ell_{p,r}}(t) \cdot p_i \cdot p_j\right)\right)p^2$$

Wherein:

$\ell_p{}^*$ is the set of all fibres $\ell_{p,r}$ passing through p; $\delta A_p(t)$ is the change in area of point p from the first frame to n's frame in time $t_n$; and $\delta A_{p,n}(t_n)$ is the determinant of the generalised strain matrix:

| $\varepsilon_{P,1}$ | $\varepsilon_{P,2}$ |
|---|---|
| $\varepsilon_{P,3}$ | $\varepsilon_{P,4}$ |

There are four strain components: $\varepsilon_{p,1}$ (x-axis direction), $\varepsilon_{p,2}$ (y-axis direction), $\varepsilon_{p,3}$ (rotation around x-axis) and $\varepsilon_{p,4}$ (rotation around y-axis).

By rewriting the new data in the generalized Lagrangian equations, following was obtained:

$$\frac{\partial L(p, \dot{p}, \varepsilon_P, \dot{\varepsilon}_P, t)}{\partial p} - \frac{d}{dt}\left(\frac{\partial L(p, \dot{p}, \varepsilon_p, \dot{\varepsilon}_p, t)}{\partial \dot{p}}\right) = \quad (3)$$
$$\sum_{\ell_{p,r} \in \ell_p} * F_{\ell_p}(p, t) = \sum_{\ell_{p,r} \in \ell_p} * \frac{\partial(\Gamma_{\ell_p} \cdot \tau_{\ell_p})}{\partial S_{\ell_p}} =$$
$$F(p, n, d_n(p), v(p, n, t), \varepsilon(p, n, t_n), \varepsilon'(p, n, t_n), t_n)$$

the Lagrangian equations can also be written as:

$$\frac{\partial L(p, \dot{p}, \varepsilon_P, \dot{\varepsilon}_P, t)}{\partial p} - \frac{d}{dt}\left(\frac{\partial L(p, \dot{p}, \varepsilon_p, \dot{\varepsilon}_p, t)}{\partial \dot{p}}\right) = \quad (4)$$
$$F(p, n, d_n(p), v(p, n, t), \varepsilon(p, n, t_n), \varepsilon'(p, n, t_n), t_n) =$$
$$\sum \left\{\frac{2d_n(p)}{t_n^2} + 2\varepsilon'(p, n, t_n) \cdot \left[\frac{\varepsilon(p, n, t_n) + 1)d_0(p)}{t_n}\right] - \frac{2v(p, n, t)}{t_n}\right\}$$

Was applied kinetic and potential energetic formulas of the cardiac segment to the left side of the Lagrangian equations:

$$\left[\partial\left[\frac{1}{2}p_1 p_2 + \frac{1}{2}\det\begin{pmatrix} \varepsilon_{p,1} & \varepsilon_{p,2} \\ \varepsilon_{p,3} & \varepsilon_{p,4} \end{pmatrix}\right]\dot{p}^2 - \quad (5)$$
$$\frac{1}{2}\left(\sum_{\ell_{p,r} \in \ell^*}\left(\sum_{1 \leq i,j \leq 2}\varepsilon_{p,i,j,\ell_{p,r}}(t) \cdot p_i \cdot p_j\right)\right)p^2\right]/\partial p\right] -$$
$$d\left(\partial\left[\frac{1}{2}\rho\left(p_1 p_2 + \det\begin{pmatrix} \varepsilon_{p,1} & \varepsilon_{p,2} \\ \varepsilon_{p,3} & \varepsilon_{p,4} \end{pmatrix}\right)\right)\dot{p}^2 -$$
$$\frac{1}{2}\left(\sum_{\ell_{p,r} \in \ell^*}\left(\sum_{1 \leq i,j \leq 2}\varepsilon_{p,i,j,\ell_{p,r}}(t) \cdot p_i \cdot p_j\right)\right)p^2\right]/\partial p/dt\right) =$$
$$\sum\left\{\frac{2d_n(p)}{t_n^2} + 2\varepsilon'(p, n, t_n) \cdot \left[\frac{(\varepsilon(p, n, t_n) + 1)d_0(p)}{t_n}\right] - \frac{2v(p, n, t)}{t_n}\right\}$$

The fourth step is to find numerical solutions to the equation which is described below in step 4 (step 4 for 2D image and 3D are same).

Development of mathematical algorithms for 3D datasets:

STEP 1: Unlike the 2D image, a 3D image is formed with a voxel. Therefore, the first step in developing a mathematical algorithm for 3D is the extraction of voxel coordinates in time and space. (FIGS. 2; 2C and 2D).

STEP 2: The second step is to extract and calculate the mechanical parameters of the original voxel. Force indices are formulated, calculated, and coded based on the extracted mechanical parameters. The force formula based on the velocity, displacement, strain, and strain rate is:

$$F(p, n, d_n(p), v(p, n, t), \varepsilon(p, n, t_n), \varepsilon'(p, n, t_n), t_n) = \tag{6}$$

$$\sum \left\{ \frac{2d_n(p)}{t_n^2} + 2\varepsilon'(p, n, t_n) \cdot \left[ \frac{(\varepsilon(p, n, t_n) + 1)d_0(p)}{t_n} \right] - \frac{2v(p, n, t)}{t_n} \right\}$$

Where: p is a 3D cardiac segment; $d_n(p)$ is the displacement of p at n's frame; $v(p, n, t)$ is its velocity at the same volume; and $\varepsilon(p, n, t_n)$, and $\varepsilon'(p, n, t_n)$ are the strain and strain rate at n's volume. The general force of p per cardiac cycle is the summation of the formula (6).

STEP 3: The third step is to design equations to find the cardiac segment (voxel) trajectory based on Lagrangian equations. Lagrangian equations for a 3D cardiac segment (point p) are described by the following reformulation based on acquired datasets:

$$L(p, \dot{p}, \varepsilon_P, \dot{\varepsilon}_P, t) = T(p, \dot{p}, \varepsilon_P, \dot{\varepsilon}_{P,t}) - U(p, \dot{p}, \varepsilon_P, \dot{\varepsilon}_P, t) = \tag{7}$$

$$\frac{1}{2}\rho[\delta \text{Volume}_{p,n}(t_n) + p_1 p_2 p_3]\dot{p}^2 -$$

$$\frac{1}{2}\left(\sum_{\ell_{p,r} \in l}\left(\sum_{1 \le i,j \le 3}\varepsilon_{p,i,j,\ell_{p,r}}(t) \cdot p_i \cdot p_j\right)\right)\dot{p}^2$$

Where:

$\ell_p{}^*$ is the set of all fibres $\ell_{p,r}$ passing through p; $\delta \text{Volume}_p(t)$ is the change in volume of point p from the first volume to n's volume in time $t_n$; and $\delta \text{Volume}_{p,n}(t_n)$ is the determinant of generalised strain matrix:

| | | |
|---|---|---|
| $\varepsilon_x$ | $\varepsilon_{xy}$ | $\varepsilon_{xz}$ |
| $\varepsilon_{yx}$ | $\varepsilon_y$ | $\varepsilon_{yz}$ |
| $\varepsilon_{zx}$ | $\varepsilon_{zy}$ | $\varepsilon_z$ |

Here, there are nine strain components: $\varepsilon_x$ (strain along the x-axis), $\varepsilon_{xy}$ (rotation around the y-axis in the xy-plane), $\varepsilon_{xz}$ (rotation around the x-axis in the xz-plane), $\varepsilon_{yx}$ (rotation around the y-axis in the xy-plane), $\varepsilon_y$(strain along the y-axis), $\varepsilon_{yz}$ (rotation around the y-axis in the yz-plane), $\varepsilon_{zx}$ (rotation around the z-axis in the xz-plane), $\varepsilon_{zy}$ (rotation around the zy-axis in the yz-plane) and $\varepsilon_z$ (strain along the z-axis).

By rewriting the new data in the generalized Lagrangian equations, following was obtained:

$$\frac{\partial L(p, \dot{p}, \varepsilon_P, \dot{\varepsilon}_P, t)}{\partial p} - \frac{d}{dt}\left(\frac{\partial L(p, \dot{p}, \varepsilon_P, \dot{\varepsilon}_P, t)}{\partial p}\right) = \tag{8}$$

-continued $$\sum_{\ell_{p,r} \in \ell_p} *F_{\ell_p}(p, t) = \sum_{\ell_{p,r} \in \ell_p} *\frac{\partial (\Gamma_{\ell_p} \cdot \tau_{\ell_p})}{\partial S_{\ell_p}} =$$

$$F(p, n, d_n(p), v(p, n, t), \varepsilon(p, n, t_n), \varepsilon'(p, n, t_n), t_n)$$

the Lagrangian equation can be written as:

$$\frac{\partial L(p, \dot{p}, \varepsilon_P, \dot{\varepsilon}_P, t)}{\partial p} - \frac{d}{dt}\left(\frac{\partial L(p, \dot{p}, \varepsilon_P, \dot{\varepsilon}_P, t)}{\partial p}\right) = \tag{9}$$

$$F(p, n, d_n(p), v(p, n, t), \varepsilon(p, n, t_n), \varepsilon'(p, n, t_n), t_n) =$$

$$\sum \left\{ \frac{2d_n(p)}{t_n^2} + 2\varepsilon'(p, n, t_n) \cdot \left[ \frac{(\varepsilon(p, n, t_n) + 1)d_0(p)}{t_n} \right] - \frac{2v(p, n, t)}{t_n} \right\}$$

Were applied kinetic and potential energetic formulas of the cardiac segment to the left side of the Lagrangian equations:

$$\left[ \partial \left[ \frac{1}{2}p_1 p_2 p_3 + \frac{1}{2}\det\begin{pmatrix} \varepsilon_x & \varepsilon_{x,y} & \varepsilon_{x,z} \\ \varepsilon_{y,x} & \varepsilon_y & \varepsilon_{y,z} \\ \varepsilon_{zx} & \varepsilon_{zy} & \varepsilon_z \end{pmatrix} \right]\dot{p}^2 - \right. \tag{10}$$

$$\frac{1}{2}\left(\sum_{\ell_{p,r} \in \ell^*}\left(\sum_{1 \le i,j \le 3}\varepsilon_{p,i,j,\ell_{p,r}}(t) \cdot p_i \cdot p_j\right)\right)\dot{p}^2 \right]/\partial p \bigg] -$$

$$d\left(\partial \left[ \frac{1}{2}\rho\left(p_1 p_2 p_3 + \det\begin{pmatrix} \varepsilon_x & \varepsilon_{x,y} & \varepsilon_{x,z} \\ \varepsilon_{y,x} & \varepsilon_y & \varepsilon_{y,z} \\ \varepsilon_{zx} & \varepsilon_{zy} & \varepsilon_z \end{pmatrix}\right)\dot{p}^2 - \right.\right.$$

$$\frac{1}{2}\left(\sum_{\ell_{p,r} \in \ell^*}\left(\sum_{1 \le i,j \le 3}\varepsilon_{p,i,j,\ell_{p,r}}(t) \cdot p_i \cdot p_j\right)\right)\dot{p}^2 \right]/\partial p/dt\bigg) =$$

$$\sum \left\{ \frac{2d_n(p)}{t_n^2} + 2\varepsilon'(p, n, t_n) \cdot \left[ \frac{(\varepsilon(p, n, t_n) + 1)d_0(p)}{t_n} \right] - \frac{2v(p, n, t)}{t_n} \right\}$$

Solutions for 2D and 3D equations:

STEP 4: The fourth step for both 2D and 3D datasets is to provide a numerical solution to the proposed equations. This solution parameterizes the cardiac segment (pixel/voxel). These new parameterizations provide smooth functions (in L2-norm functional spaces) attached to the cardiac segment (pixel/voxel) trajectory detections. Were designed equations corresponding to each pixel/voxel and based on Lagrangian mechanics. It could be numerically solving this algorithm of partial differential equations. A function (belonging to L2-norm functional space) was created for each pixel/voxel: $f_p$, f sub pixel, $f_v$, f sub voxel.

Figure 3A:
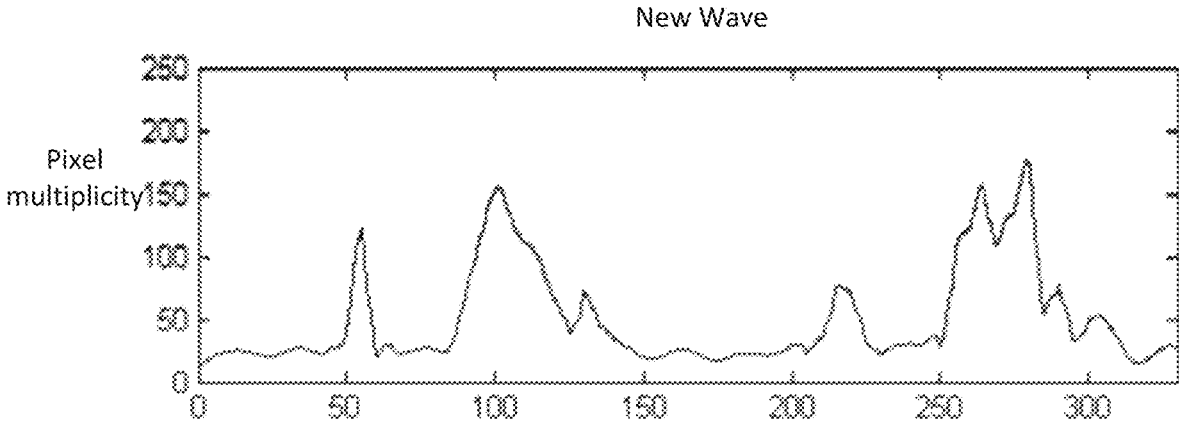
FIG. 3A shows a reconstructed wave corresponding to the 2D reversal wave shown in FIG. 2A; in the reconstructed wave, the number of pixels and cardiac phases increases, the vertical axis is the new pixel multiplicity, and the horizontal axis is the number of new cardiac phases, according to an exemplary embodiment of the present invention.
Figure 3B:
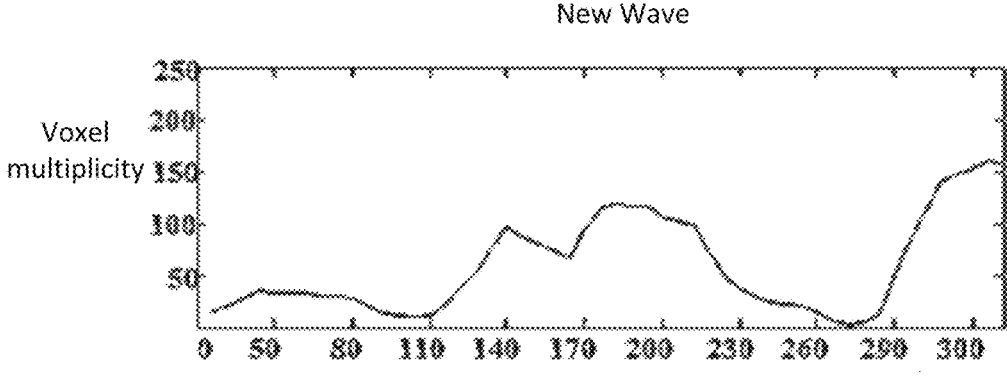
FIG. 3B shows a reconstructed wave corresponding to the 3D reversal wave shown in FIG. 2A, the number of voxels and volume increases; the vertical axis is the voxel multiplicity, and the horizontal axis is the number of new volumes.

New 2D curvelets attached to each pixel are reconstructed. A pixel is then presented as a 2D wedge with considerations for longitudinal, radial, and angular tensions (rotations). New curvelet coefficients are introduced and quantified by inner products between $f_p$ and $\varphi_p$ (Fourier coefficients of the original image datasets attached to the point p) $f_p \cdot \varphi_p$ (FIG. 3, 3A).

As in 2D, new 3D curvelets linked to each voxel are reconstructed. A voxel is presented as a 3D wedge and, as with 2D, longitudinal, radial, angular, and circumferential directions are calculated. New curvelet coefficients are introduced and quantified by inner products between $f_v$ and $\varphi_v$ (Fourier coefficients of the original image datasets attached to the point v) $f_v \cdot \varphi_v$ (FIG. 3; 3B). The new 2D and 3D curvelets present new 2D images and 3D full volumes.

Processing the Coding Algorithms:

Once acquired from the 2D/3D echography system, the patient's echo datasets are loaded into the C++-coded image-processing program. Echo datasets are read and wave datasets, including Fourier coefficients and initial mechanical parameters, are stored.

Figure 4:
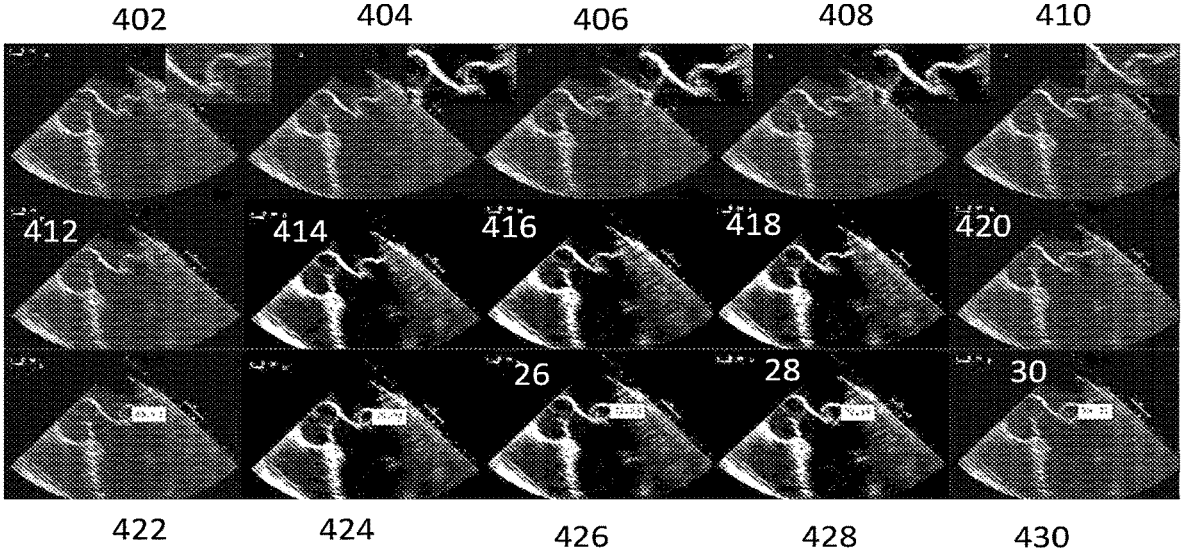
FIG. 4 shows images of two original cardiac phases (402, 410) that are fixed; three new reconstructed cardiac phases (404, 406, 408) between (402) and (410); Two original cardiac phases (412, 420); three new cardiac phases after 2D rendering by the disclosed system (414, 416, 418), with high intensity resolution increasing; calculated distances (422, 424, 426, 428, 430) show the numerical increase in spatial resolution.
Figure 5:
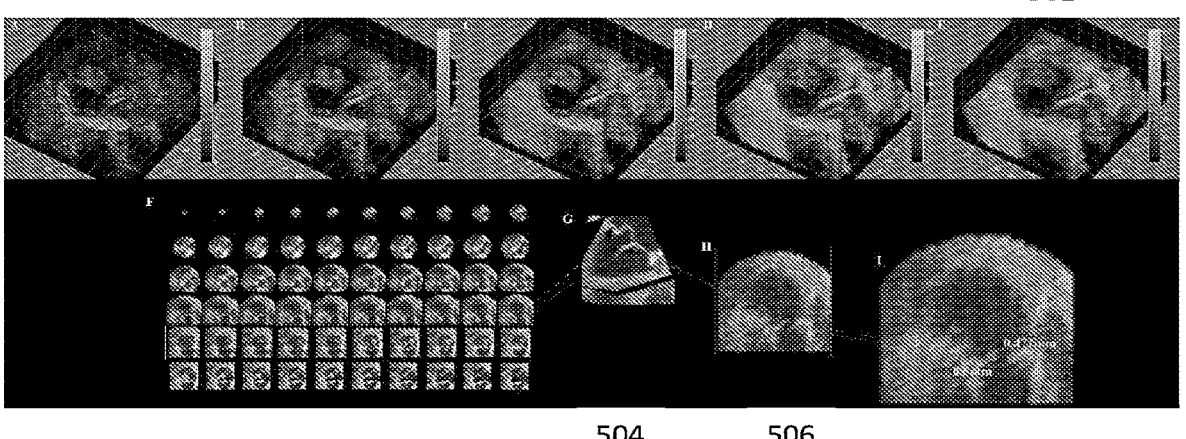
FIG. 5 shows an increase in spatial and temporal resolution for 3D echocardiography, according to an exemplary embodiment of the present invention, top row are 3D view of the mitral valve, wherein voxels increase with the creation of each new volume; image 502 shows each volume is formed by different sections, each section is made with increasing voxel creation, here two hundred and four sections are glued together to make each volume; in image 504 3D mitral valve is represented by its 2D vertical and horizontal slice, here one slice is shown; in image 506 selected is a section and two areas of interest.
Figure 6:
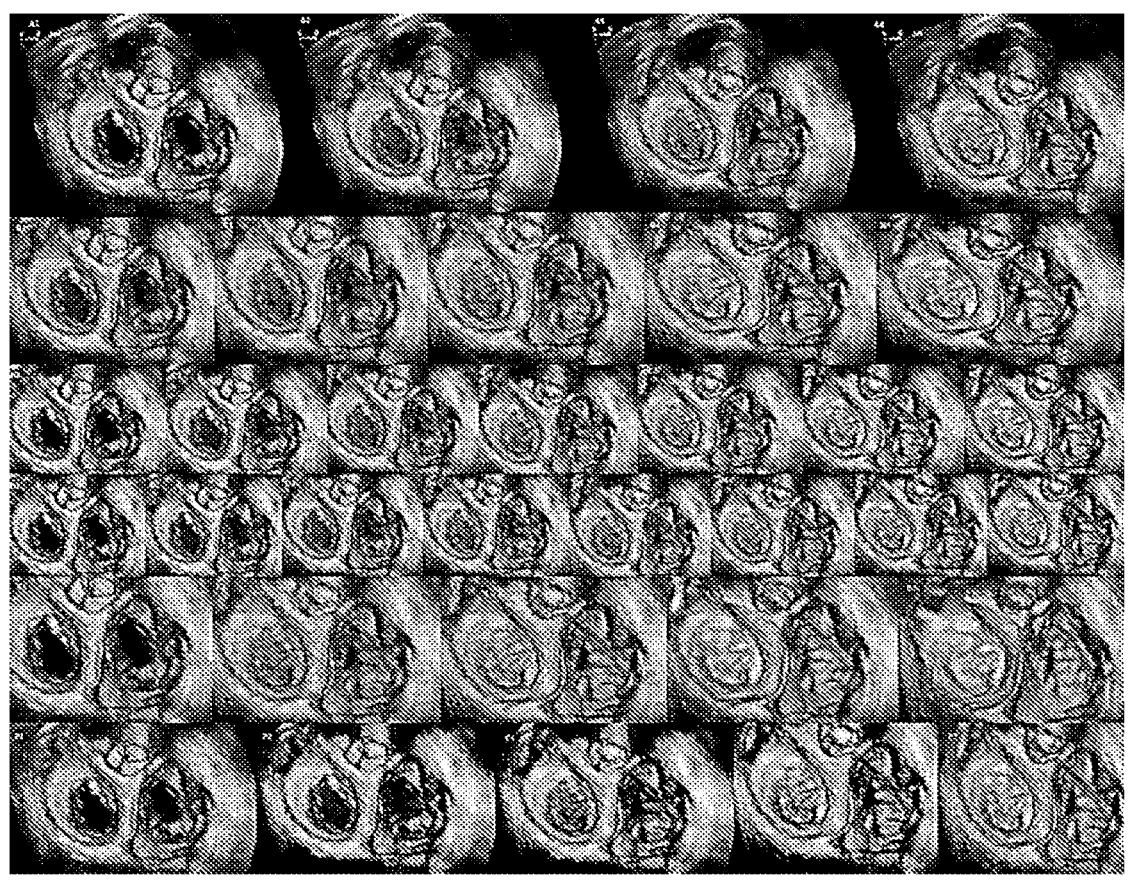
FIG. 6 are the images showing the mathematical programming of the 3D view of the aortic, mitral, and tricuspid valves. Images in the top row shows increasing number of voxels and volumes between two fixed original volumes and Leaflet motions are visible in the new volumes; images in the second row shows increasing number of voxels and volumes by multiplying step 6 between two fixed volumes of (b1) and (b5) (left to right), also leaflet motions are visible in new volumes; third row shows the increased number of voxels and volumes by multiplying step 8 between two fixed volumes (c1) and (c7) (left to right), also leaflet motions are visible by eye in new volumes. Fourth row shows the increased number of voxels and volumes by multiplying step 10 between two fixed volumes (d1) and (d8) (left to right). Leaflet motions are visible by in new volumes; (e2-e4)

The coefficients of the original waves and diagrams are read and calculated. The number of original cardiac phases/volumes is also calculated. Calculated coefficients translate to the mechanical parameters of a pixel or voxel per cardiac cycle. The force index resulting from motions and deformations was formulated and calculated. Original motion and deformation indices near the force data were entered into the Lagrangian equations to extract multiple locations for each pixel or voxel in different phases, from the end of diastole to the end of systole, within a cardiac cycle. Solutions are coded as functions in L2 norm spaces. These functions are referred to as $f_p$ for each echocardiographic segment. Fourier coefficients $f_p$ are calculated. Inner products between Fourier coefficients of original reversal waves $\varphi_p$ with the coefficients of $f_p$ introduce a new series for each point p. By applying the inverse Fourier transform on the obtained series can be created new curvelet datasets (FIG. 3). Therefore, the newly reconstructed waves can be converted into images with increase in the spatial resolution such that two near points are distinguishable by less than one millimeter (FIG. 4 for 2D and FIG. 6 for 3D). The actual increase in pixels and voxels is depicted in FIG. 5; 5A-I. The number of increased voxels is visible and stored in the output folder of the program for each multiplying step. New waves and images are then reconstructed based on frame and volume increases (FIG. 4 for 2D and FIG. 6 for 3D).

Referring to the FIG. 7-FIG. 17

Echocardiography emits high-frequency sound waves onto cardiac tissue, interpreting their reflection as images. In fact, the scattering ultrasonic waves, the reversal waves, carry a lot of information to create images. These reversal waves are input for mathematical equations. After solving these equations, echocardiographic images are formed based on the Fourier series. In other words, an echocardiographic image is a solution of these equations of reversal waves. By putting these solutions together side by side, the movement of the heart is observed in the cardiac cycle and a video file is created.

Therefore, conceptually, an image or a frame in a cardiac phase corresponds to a set of solutions from the equations of reversal waves. For a simple understanding of the basis of mathematical solution in this manuscript—which is based on ultrasonic reversal waves—it is consider a set of solutions of wave equations as the images (detailed mathematical equations is explained in methodology). Hence, in the following general description of the mathematical solution, instead of a set of solutions of wave equations, images are used as analogy that corresponds to these solutions.

A raw two-dimensional echocardiography video is acquired. 2D raw images or frames are extracted from the video. A typical 2D echocardiographic video file consists of different frames, and each frame is made of multiple pixels (FIG. 7A; 7B). Each pixel represents an anatomical point in the heart that is tracked in a cardiac cycle. These anatomical points are represented geometrically by pixels on a two-dimensional Cartesian coordinate system (FIG. 7A; 7B). Because the points in the heart are moving, these pixels also move on the coordinate plane (FIG. 7A; 7A), and the study of the motion and deformation of these pixels corresponds to the movements of the anatomical points of the heart.

Based on the motion and deformation of anatomical points in the raw echocardiographic input data, the corresponding original velocity and strain of the pixels can be calculated on the Cartesian coordinate plane. According to Newton's second law, the calculation of the force that leads to motion and deformation is very important. Therefore, the force index in terms of velocity and strain is formulated (formulations with details were calculated in above referring to FIG. 1). The initial amount of the force can be measured in terms of the initial velocity and strain obtained from velocity vector tracking. These values are entered into Lagrangian equations to obtain the trajectories achieved by the selected pixels according to Lagrange law in physics (mathematical details can be found in the methods).

Conversely, each frame consists of several pixels, for example N pixels. Therefore, each frame can easily be considered equivalent to an ordered N-tuples FIG. 8 This shows that each frame can be placed in a Euclidean N-dimensional space. The maximum and minimum values of the distances and the change of angles from the end of the diastole to the end of the systole can be determined (tracking code). Therefore, can be drawn spheres based on these values around the frames which are points in the N-dimensional space FIG. 9.

Because the heart is elastic, the distance, angles, and deformation between the anatomical points in the heart do not change in a cardiac cycle. It can be defined a mapping "f" ($f_p$'s) from this N-dimensional space and the spheres drawn into the 3D Cartesian coordinate space so that the values of this mapping are compatible with the trajectories obtained by solving the Lagrangian equations. This mapping f (FIG. 10)—which is based on pixel tracking and the trajectories obtained by the Lagrange equations—provides precise absolute in-plane real-time biomechanical parameters of any anatomic point in the heart during the full cardiac cycle like velocities, strains, forces, divergences, vortices, lengths, distances, angels and a fiber bundle of $l_p$'s that represents flow movements (optimized trajectories) of each cardiac points 'p' in the heart per a cardiac cycle. Furthermore, these precise in-plane mechanical events are fused with geometrical points (FIG. 11, FIG. 12, FIG. 13, FIG. 14).

For the 3D mode (FIG. 15), a voxel replaces instead of a pixel and the mathematical workflow is the same as above, with the key difference that mapping occurs in a Cartesian 3D space which preserves rotational indices and compatibles with Lagrange equations in terms of 3D motion and strain data (mathematical details can be found in the methods). An additional consequence of this model is that one can retrieve unlimited number of cardiac phases and volumes between existing cardiac phases and volumes visualized in echocardiographic images. Furthermore, using K-theory in algebraic geometry any structure of the heart can be tracked as separate entity for virtual simulation.

In another case was applied mathematical algorithms on 3D surgical view of the mitral valve. Original frames of 12 were increased to 120. Were traced 60 points on the annulus of the mitral valve and tracked the velocity vectors throughout the cardiac cycle. By using K-theory in algebraic geometry different structures of the mitral valve could be tracked throughout the cardiac cycle (FIG. 16).

In another case, were applied mathematical algorithms on long-axis view of the heart on 2D TEE. Here was increased the number of frames from 66 to 660. Over 120 points were selected for which the velocity vectors were tracked throughout the cardiac cycle. By using K-theory methods in algebraic geometry, could track the mitral apparatus including the native chords throughout the cardiac cycle (FIG. 17).

A voxel tracking in a single full heartbeat acquisition was detected for five selected points; Second row (a6-a10) FIG. 18: Colour coding for 3D strain; red for negative values, green for positive values. Coloured spectrums change between green and red. In another voxel tracking case, the mathematical algorithms were applied on 3D surgical view of the mitral valve annulus FIG. 19.

Pixel tracking were also studied to follow blood velocity vectors (green vectors) inside the left ventricular cavities (FIG. 20-FIG. 22). In another case, mathematical algorithms were applied on long-axis view of the heart on 2D TEE under the level of aortic valve and aortic wall. Pixie tracking were also tracked to study the perturbation blood velocity vectors inside the aortic wall FIG. 23.

For experimentation, the disclosed method was evaluated for several complicated cases as shown in FIGS. 24-26.

FIG. 27 illustrate an advantageous feature of the disclosed method, wherein the heart geometrical indices can be automatically calculated over the real time for each cardiac phase.

One of the advantageous of our methods is based on the combination of K-theory and Lagrangian equations. In this way, for example, two arbitrary points on the heart mitral valve annulus was selected. The distance to these two points is the shortest curve that connects these two points which is the critical point of the Lagrangian energy integral between those two points. With this method, one can calculate the length between any two traced points. Moreover, by differentiating the second order of the energy integral function, we enter to the Jacobi computational field. This makes it possible to calculate the smallest variation between two selected points while moving on the bend between the two points. This provides it possible to determine the actual bend that changes during the vibration between the two points and calculate its length which is particularly important during mitral valve repair.

FIG. 28 shows an architecture of the disclosed system 2800 having a processor 2810 and a memory 2820. The processor can be any logic circuitry that responds to, and processes instructions fetched from the memory. The memory may include one or more memory chips capable of storing data and allowing any storage location to be directly accessed by the processor. The memory includes modules according to the present invention for execution by the processor to perform one or more steps of the disclosed methodology. The memory can include an algorithm module 2830, a development module 2840, and a testing module 2850.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above-described embodiment, method, and examples, but by all embodiments and methods within the scope and spirit of the invention as claimed.

What is claimed is:

1. A method for creating a virtual human heart model for clinical applications, the method implemented within a system comprising a processor and a memory, the method comprises:

receiving, from a cardiac echocardiography system, a 2D or 3D echo dataset comprising ultrasound reversal wave data acquired from a heart of a patient;

retrieving from the echo dataset a plurality of 2D or 3D echo images or video clips;

converting the plurality of 2D or 3D echo images or video clips to a plurality of pixel or voxel data;

tracking, by the processor, an arbitrary pixel or voxel in the plurality of pixel or voxel data phase-by-phase per cardiac cycle to determine motion of a corresponding anatomical point of the heart;

determining, for the arbitrary pixel or voxel, an original reversal wave equation $\rho_p$ based on the ultrasound reversal wave data;

generating, by solving Lagrange-Euler equations, a deformable map $f_p$ the arbitrary pixel or voxel within the cardiac cycle;

determining, based on the deformable map $f_p$ and the original reversal wave equation $\rho_p$ curvelet coefficients associated with the arbitrary pixel or voxel;

reconstructing, using the curvelet coefficients, new 2D or 3D images comprising additional cardiac phases or volumes not present in the echo dataset; and forming, from the new 2D or 3D images, a dynamic virtual heart model of the patient with improved spatial resolution for use in diagnosis or treatment planning.

2. The method according to claim 1, wherein the 2D or 3D echo dataset is present in DICCOM file format.

3. The method according to claim 1, wherein the method further comprises:

extracting first coordinates of the arbitrary pixel positions in time and space;

calculating, mechanical parameters of the original pixel or voxel, wherein the mechanical parameters comprise velocity and strain; and calculating force indices from the velocity and strain.

4. The method according to claim 1, wherein the method further comprises:

generating a virtual heart model of a heart having enhanced resolution and depicting all movements in the heart, wherein pixels in the plurality of pixel data represent anatomical points in the heart.

5. The method according to claim 4, wherein the method further comprises:

Distinguish structures of the virtual heart model, in a cardiac cycle, using different colors by applying K-theory in algebraic geometry.

6. The method according to claim 4, wherein the method further comprises:

generating new cardiac phases or volumes between existing cardiac phases or volumes as visualized in the plurality of 2D or 3D echo images or video clips.

7. The method according to claim 1, wherein the method further comprises:

determining new quantitative data comprising motion and deformation for the arbitrary pixel or voxel.

8. The method according to claim 7, wherein the method further comprises:

reformulating a geometrical index "Curvature" based on the 3D echo datasets, wherein the curvature is color codes, the curvature in different states has different colors.

9. A system for human heart modelling, the system comprising a processor and a memory storing instructions, the processor being configured to execute the instructions to:

receive, from a cardiac echocardiography system, a 2D or 3D echo dataset comprising ultrasound reversal wave data acquired from a heart of a patient;

retrieve from the echo dataset a plurality of 2D or 3D echo images or video clips;

convert the plurality of 2D or 3D echo images or video clips into pixel or voxel data representing anatomical points of the heart;

track an arbitrary pixel or voxel in the pixel or voxel data phase-by-phase through a cardiac cycle to determine motion of the corresponding anatomical point;

determine, for the arbitrary pixel or voxel, an original reversal wave equation $\rho_p$ based on the ultrasound reversal wave data;

generate, by solving Lagrange-Euler equations, a deformable map $f_p$ representing a trajectory of the arbitrary pixel or voxel within the cardiac cycle;

determine curvelet coefficients based on the deformable map $f_p$ and the original reversal wave equation $\rho_p$;

reconstruct, using the curvelet coefficients, new 2D or 3D images comprising additional cardiac phases or volumes not present in the echo dataset; and form, from the new 2D or 3D images, a dynamic virtual heart model of the patient having improved spatial resolution for use in diagnosis or treatment planning.

10. The system according to claim 9, wherein the 2D or 3D echo dataset is stored in a DICCOM file format.

11. The system according to claim 9, wherein the processor is further configured to:

extract first coordinates of the arbitrary pixel or voxel positions in time and space;

calculate, mechanical parameters of the original pixel or voxel, wherein the mechanical parameters comprise velocity and strain; and calculate force indices based on the velocity and strain.

12. The system according to claim 9, wherein the processor is further configured to generate a virtual heart model comprising high-resolution representations of cardiac structures and movements, wherein each pixel or voxel corresponds to an anatomical point in the patient's heart.

13. The system according to claim 12, wherein the processor is further configured to distinguish different cardiac anatomical structures throughout a cardiac cycle using color coding, the color coding based on K-theory in algebraic geometry.

14. The system according to claim 12, wherein the processor is further configured to generate new cardiac phases or volumes between existing cardiac phases or volumes represented in the original 2D or 3D echo dataset.

15. The system according to claim 9, wherein the processor is further configured to determine new quantitative biomechanical parameters for the arbitrary pixel or voxel, the biomechanical parameters comprising motion and deformation metrics.

16. The system according to claim 15, wherein the processor is further configured to reformulate and calculate a geometrical curvature index based on the 3D echo dataset, wherein the curvature for different states is color-coded on the virtual heart model.

* * * * *